(12) United States Patent
Sakakibara et al.

(10) Patent No.: US 7,334,780 B2
(45) Date of Patent: Feb. 26, 2008

(54) DEVICE AND METHOD FOR MANUFACTURING CARBONATED SPRING AND CARBONIC WATER, CONTROL METHOD FOR GAS DENSITY APPLIED THERETO AND MEMBRANE MODULE

(75) Inventors: Hiroki Sakakibara, Tokyo (JP); Ken Ooyachi, Aichi (JP); Hiroshi Tasaka, Aichi (JP)

(73) Assignee: Mitsubishi Rayon Company, Limited, Minato-ku, Tokyo (JP)

( * ) Notice: Subject to any disclaimer, the term of this patent is extended or adjusted under 35 U.S.C. 154(b) by 0 days.

(21) Appl. No.: 11/802,496

(22) Filed: May 23, 2007

(65) Prior Publication Data
US 2007/0222090 A1 Sep. 27, 2007

Related U.S. Application Data

(62) Division of application No. 11/506,843, filed on Aug. 21, 2006, now Pat. No. 7,237,767, which is a division of application No. 10/487,917, filed as application No. PCT/JP02/08594 on Aug. 27, 2002, now Pat. No. 7,152,850.

(30) Foreign Application Priority Data

| Aug. 28, 2001 | (JP) | ............................. 2001-257737 |
| Feb. 14, 2002 | (JP) | ............................. 2002-036917 |
| Jun. 20, 2002 | (JP) | ............................. 2002-180143 |
| Jun. 20, 2002 | (JP) | ............................. 2002-180144 |
| Jul. 17, 2002 | (JP) | ............................. 2002-208575 |

(51) Int. Cl.
*B01F 3/04* (2006.01)

(52) U.S. Cl. ................ 261/36.1; 361/104; 361/DIG. 7; 73/19.03; 73/629; 73/861.25; 73/861.41

(58) Field of Classification Search ............. 261/36.1, 261/37, 38, 42, 94, 95, 96, 100, 101, 102, 261/104, 107, 121.1, 122.1, DIG. 7; 73/19.03, 73/19.04, 19.1, 627, 629, 630, 861.04, 861.25, 73/861.41

See application file for complete search history.

(56) References Cited

U.S. PATENT DOCUMENTS 5,157,930 A 10/1992 McGhee et al.

(Continued)

FOREIGN PATENT DOCUMENTS

EP 0 732 142 A2 9/1996

(Continued)

OTHER PUBLICATIONS

Macht Christian, "Herstellung ultradü nner Polymerfilme und Untersuchung ihrer Gastrenneigenschaften," [Online], Dissertation, Tu Berlin (Sep. 14, 2000), XP-002389159.

*Primary Examiner*—Scott Bushey
(74) *Attorney, Agent, or Firm*—Fitch Even Tabin & Flannery

(57) ABSTRACT

Hot water (12) in a bath (11) is pumped up by a suction pump (9) and introduced into a carbon dioxide gas dissolver (7) through solution flow rate adjusting means (14) and then, poured into the bath (11). Carbon dioxide gas supplied from a carbon dioxide gas cylinder (1) is introduced into the carbon dioxide gas dissolver (7) through gas flow rate adjusting means (5). At this time, the quantity of bubbles existing in artificial carbonated spring in a take-out pipe (15) is measured with a measuring device (13), and the solution flow rate adjusting means (14), gas flow rate adjusting means (5) and the like are controlled by means of a control device (16) using a relational expression between a preliminarily set quantity of bubbles and carbon dioxide concentration to obtain a desired concentration of carbon dioxide gas in carbonated spring. Because the carbon dioxide gas flow control means (5) is provided between the carbon dioxide gas dissolver (7) and a carbon dioxide gas supply source, carbonated spring of a high concentration can be always manufactured even if the pressure of supplied carbon dioxide gas changes or the permeating performance of a membrane changes.

8 Claims, 6 Drawing Sheets

U.S. PATENT DOCUMENTS

| | | | |
|---|---|---|---|
| 5,210,172 | A | 5/1993 | Van Hout et al. |
| 5,356,533 | A | 10/1994 | Nakagawa |
| 5,403,088 | A | 4/1995 | Killmer et al. |
| 5,945,039 | A | 8/1999 | Kojima |
| 6,158,721 | A | 12/2000 | Katou et al. |
| 6,164,632 | A | 12/2000 | Uchida et al. |
| 6,905,111 | B2 | 6/2005 | Nagasaka et al. |
| 7,152,850 | B2 * | 12/2006 | Sakakibara et al. ........ 261/36.1 |
| 7,237,767 | B2 * | 7/2007 | Sakakibara et al. ........ 261/36.1 |
| 7,246,793 | B2 * | 7/2007 | Nagasaka et al. .......... 261/36.1 |
| 2004/0154374 | A1 * | 8/2004 | Daw et al. ................... 73/1.02 |

FOREIGN PATENT DOCUMENTS

| | | |
|---|---|---|
| EP | 0 732 142 A3 | 6/1998 |
| EP | 1 283 069 A1 | 2/2003 |
| GB | 2 261 383 A | 5/1993 |
| GB | 2 351 243 A | 12/2000 |
| JP | 2-279158 A | 11/1990 |
| JP | 7-114790 B2 | 12/1995 |
| JP | 07-328403 | 12/1995 |
| JP | 8-2415 B2 | 1/1996 |
| JP | 8-158774 A | 6/1996 |
| JP | 8-215270 A | 8/1996 |
| JP | 10-015368 A | 1/1998 |
| JP | 10-277121 A | 10/1998 |
| JP | 11-139804 A | 5/1999 |
| JP | 2000-5586 A | 1/2000 |
| JP | 2000-159504 A | 6/2000 |
| JP | 3168135 B2 | 3/2001 |
| JP | 2001-113289 A | 4/2001 |
| JP | 2001-293344 A | 10/2001 |
| SU | 1 676 438 A3 | 9/1991 |
| WO | WO 01/78883 A1 | 10/2001 |

* cited by examiner

DEVICE AND METHOD FOR MANUFACTURING CARBONATED SPRING AND CARBONIC WATER, CONTROL METHOD FOR GAS DENSITY APPLIED THERETO AND MEMBRANE MODULE

This Application is a Rule 1.53(*b*) Divisional Patent Application of U.S. patent application Ser. No. 11/506,843 filed Aug. 21, 2006, now U.S. Pat. No. 7,237,767, which was a Divisional Patent Application of U.S. application Ser. No. 10/487,917 filed Feb. 27, 2004, now U.S. Pat. No. 7,152,850 which was the U.S. National Phase Application under 35 U.S.C. 371 of International Application No. PCT/JP2002/08594 filed Aug. 27, 2002, and claims the priority from Japanese Application No. 2001-257737 filed Aug. 28, 2001, Japanese Application No. 2002-36917 filed Feb. 14, 2002, Japanese Application No. 2002-180144 filed Jun. 20, 2002, Japanese Application No. 2002-180143 filed Jun. 20, 2002, and Japanese Application No. 2002-208575 filed Jul. 17, 2002, the complete disclosures of which are incorporated herein by reference.

TECHNICAL FIELD

The present invention relates to a device and method for manufacturing carbonated spring and carbonic water. More specifically, the present invention relates to a device and method for manufacturing carbonated spring and carbonic water having a high concentration in order to always obtain a predetermined carbonic acid concentration effectively. Further, the present invention relates to a method for measuring the gas concentration of a gas dissolved solution obtained by dissolving gas into a liquid and a device for manufacturing the solution. More particularly, the present invention relates to a method for controlling the gas concentration in the solution manufactured continuously to a desired concentration and a device for manufacturing a preferable gas dissolved solution and a membrane module for dissolving gas into the liquid effectively.

BACKGROUND ART

Solution in which gas is dissolved is used for various kinds of application. If exemplifying carbon dioxide gas as a gas, weak carbonic water having a low carbon dioxide gas concentration, carbonic beverage whose carbon dioxide gas concentration is intensified under a high pressure, artificial carbonated spring in which carbon dioxide gas is dissolved in hot water, carbon dioxide dissolved solution used for industrial purpose and the like have been widely used.

Generally, hot spring effects such as blood vessel expansion effect gained in taking bath in hot water containing carbon dioxide gas such as carbonated spring and difficulty of chilling after bath have been well known and utilized in public springs and the like using hot spring since before. The keeping warm effect of the carbonated spring is, basically, considered to be because the physical environment is improved by distal blood vessel expansion effect of contained carbon dioxide gas. Further, carbon dioxide enters the skin so that capillary beds are increased and expanded thereby improving circulation of blood in the skin. Thus, it is considered that this has an effect in cure on regressive disease and distal circulation trouble. Further, a curative effect under a high concentration of about several hundreds mg/l to 1,000 mg/l has been verified in recent years. For the reasons, chemicals and devices capable of providing carbonic water for bath easily have been marketed.

To obtain such carbonated spring artificially, a chemical method for allowing carbonate to react with acid, a method by using combustion gas from a boiler, a device for blowing carbon dioxide gas directly into a pipe having a throttle as disclosed in Japanese Patent Application Laid-Open NO. 5-238928, a method by using a static mixer as a carbon gas dissolver as disclosed in Japanese Patent Application Publication Nos. 7-114790 and 7-114791, and the like are available.

Recently, many methods for producing carbonated spring by using a membrane have been proposed. For example, Japanese Patent No. 2810694 uses a hollow yarn membrane module incorporating plural porous hollow yarn membranes whose both ends are open and further, Japanese Patent Nos. 3048499 and 3048501, Japanese Patent Application Laid-Open No 2001-293344 and the like have proposed methods of using a nonporous hollow yarn membrane as a hollow yarn membrane.

As a method for producing carbonated spring using a membrane, a so-called one-pass type in which carbonated spring is produced by passing raw water through a carbon dioxide gas dissolver having a membrane module once and a so-called circulation type in which hot water is circulated in a bath through a carbon dioxide gas dissolver using a circulation pump are available.

Meanwhile, the method by using the porous hollow yarn membrane has such a fear that the membrane turns hydrophilic due to a long term usage so that water leaks to the gas side to seal the membrane surface, thereby initial carbon dioxide gas adding ability is eliminated. Contrary to this, if the nonporous hollow yarn membrane is used, the nonporous membrane exists between the gas side and the liquid side, so that no water may leak to the gas side despite a long term usage. However, there is a fear that because water vapor which is water molecular passes, the passing water vapor is condensed on the gas side, thereby the condensed water (drain) seals the membrane surface.

Thus, according to the Japanese Patent Application Laid-Open Nos. 7-313855 and 7-328403, a drain release valve is disposed on the gas side and the valve is opened/closed periodically to discharge drain from the gas side. However, according to this method, the drain release needs to be carried out frequently for a membrane in which the amount of passing vapor is large and thus, carbon dioxide gas charged on the gas side needs to be discharged into the atmosphere, and therefore, the amount of consumption of carbon dioxide gas is likely to be increased.

On the other hand, if the carbonated spring is produced according to the method by using the membrane, there is a disadvantage that the same carbon concentration cannot be secured each time although the carbonated spring having a high concentration can be obtained most highly effectively. Particularly, if the carbonated spring is produced a number of times continuously on the same day, a phenomenon that the carbonic acid concentration drops in the initial period of carbon dioxide gas passage occurs.

According to the above-described methods, although flow rate and pressure are indicated for control of carbon dioxide gas, only the flow rate is controlled under the pressure control using a pressure control valve or the like which is used by being directly connected to a gas cylinder as indicated in many of the embodiments. Thus, the flow rate of the carbon dioxide gas passing through the membrane differs between the initial period of the passage and its stabilizing period. The reason why the flow rate of the carbon dioxide gas changes is considered to be that because the membrane is cooler than the water temperature in the initial period and the concentration of carbon dioxide gas in the membrane is low, the carbon dioxide is unlikely to pass through the membrane even under the same pressure. However, if carbonated spring having some appropriate concentration is produced, there is no any problem at that time and not so much attention is paid to the accuracy.

However, in case of carbonated spring in the vicinity of a carbon dioxide gas saturated concentration at 40° C., which is around 1200 mg/l, it has been made evident that in terms of its curative effect, a further remarkable effect can be expected and there is no way but changing a though that everything is satisfied if carbonated spring having an appropriate concentration is produced. Thus, a necessity of producing the carbonated spring with a high concentration and excellent reproducibility is generated. On the other hand, the above-mentioned carbon dioxide gas dissolver has been modified frequently so that improvement of carbon dioxide gas dissolving efficiency has been tried gradually. However, a further improvement in the dissolving efficiency has been demanded. Particularly in a full-body bathing device which uses a large amount of carbon dioxide gas, the improvement in the dissolving efficiency is important.

Even a method using pressure control is capable of producing carbonated spring having a high concentration if an operation method by providing with an allowance is used, for example, by setting a slightly excessively high pressure or increasing the operation time in case of a circulation type. However, if such a method is applied, carbon dioxide gas is consumed wastefully, which is not preferable.

Further, in case of application for hospitals, a method of producing high-concentration carbonated spring in as short a time as possible has been demanded in order to care as many patients as possible. However, the circulation type has such a disadvantage that the time for producing the high-concentration carbonated spring is prolonged because no sufficient flow rate is secured in the initial period.

On the other hand, the method for producing carbonated spring with an excellent reproducibility by using the one-pass type has been described in Japanese Patent Application Laid-Open No. 10-277121. According to this method, the concentration of carbon dioxide gas in the produced carbonated spring is measured and by feeding back the concentration, the quantity of carbon dioxide gas supplied is controlled. For the reason, it takes a long time to reach a target carbon dioxide gas concentration. Further, this method has such a disadvantage that if alkali degree of raw water changes, no excellent reproduction can be attained.

Examples of the method for measuring the concentration of gas in a gas dissolved solution include a method for measuring the gas concentration by using a gas concentration measuring device of ion electrode type, a method for measuring the gas concentration by measuring pH after preliminarily measured alkaline degrees are programmed, a method for measuring the gas concentration electrochemically after the pH value of a solution is adjusted by adding chemical to the solution, a method for measuring the gas concentration according to thermal conductivity of gas discharged by adding chemical to a solution, a method for measuring the gas concentration according to infrared ray absorption ratio of a solution, a method for measuring the gas concentration by detecting the pressure of gas discharged from a solution when ultrasonic wave is applied thereto (Japanese Patent Application Laid-Open No. 5-296904) and the like.

However, according to the above-described gas measuring method, since its operation is very complicated and upon usage, it takes a large number of time and labor, the concentration of gas in absolution produced continuously from a dissolver cannot be measured on time.

Hereinafter, artificial carbonated spring will be described as an example of solution. Generally, the artificial carbonated spring is produced as artificial carbonated spring by dissolving carbon dioxide gas of a predetermined concentration in hot water. Because it is considered that the artificial carbonated spring has an excellent effect upon distal blood circulation trouble by its strong blood vessel expanding action, it has been widely used for cure and hot spring cure. Although carbonated spring spouted naturally is used up to now, currently, the artificial carbonated spring cure has been widely used as one internal medicine cure due to development of the excellent artificial spring production method.

From the clinical research result in the artificial carbonated spring cure, it has been made evident that the effective concentration of carbon dioxide gas usable for cure becomes max from 1,000 mg/l to about 1,400 mg/l. Additionally, it has been indicated that responsibility to the carbon dioxide gas concentration differs depending on the degree of seriousness of disease and continuation period of cure. In actual artificial carbonated spring cure, it is necessary to set an appropriate concentration of carbon dioxide gas corresponding to a patient.

Thus, if the artificial carbonated spring is used for cure, the concentration of carbon dioxide gas dissolved in a solution is an important factor. The artificial carbonated spring of a predetermined concentration produced continuously with a dissolver requests to take bath just after it is stored in a storage bath. If it takes long for measurement of the concentration of gas in the artificial carbonated spring, carbon dioxide gas in the storage bath is emitted into the atmosphere so that the concentration of gas in the artificial carbonated spring drops. If a patient takes a bath in this condition, he/she cannot take bath under a desired carbon dioxide gas concentration so that the curative effect by the artificial carbonated spring cannot be expected. Further, when necessity of measuring the gas concentration a number of times repeatedly exists, it comes that the temperature of hot water itself drops.

Particularly, if the carbon dioxide gas concentration is measured according to the ion electrode type method, it takes several minutes until a measuring result is obtained, so that the measuring result cannot be obtained in a short time because several minutes is always needed for each measurement. Further, according to the method of measuring the carbon dioxide gas concentration by measuring pH after the alkaline degree is programmed preliminarily, it is necessary to measure an alkaline degree preliminarily in each case, the alkaline degree different depending on water quality. Moreover, if other ion or salt is mixed, the alkaline degree needs to be measured again, and to obtain a response result of the pH measurement, it takes some time. Thus, the carbon dioxide gas concentration cannot be measured in line at the same time when the artificial carbonated spring is produced.

On the other hand, examples of the method for producing the artificial spring include a method of dissolving bubbles of carbon dioxide gas generated by chemical reaction in hot water (Japanese Patent Application Laid-Open No. 2-270158), a method of filling hot water in a pressure tank with carbon dioxide gas under a high pressure, a method of mixing carbon dioxide gas with hot water forcibly by an agitator called static mixer in a diffuser provided halfway of a hot water conduit (Japanese Patent Application Laid-Open No. 63-242257), a method by using a multi-layer composite hollow yarn membrane dissolver ("Carbonic Water Producing Device MRE-SPA" made by Mitsubishi Rayon Engineering Co., Ltd.), and the like.

The methods by using the static mixer or multi-layer composite hollow yarn membrane dissolver are suitable for production of a large amount of the artificial carbonated spring continuously and by passing hot water through the carbon dioxide gas dissolver repeatedly by means of the circulation path, the concentration of the carbon gas can be raised gradually up to a predetermined concentration.

In case of producing artificial carbonated spring continuously, artificial carbonated spring having a predetermined carbon dioxide gas concentration can be produced by combining the carbon dioxide gas concentration measuring means with the artificial carbonated spring manufacturing method. However, the case of producing the artificial carbonated spring continuously in line has a problem in response velocity in the method for measuring the concentration of carbonated oxide gas. Although measurement based on the ion electrode method is a general method as a method for measuring the concentration of carbon dioxide gas in water, its response velocity is slow and particularly, a solution whose carbon gas dioxide concentration is 1000 to 1400 mg/l, required for the artificial carbonated spring takes long hours for the ion electrode to be balanced. Further, because gas bubbles adhere to the ion electrode thereby disabling accurate measurement, the measurement in line and on time is difficult to achieve.

Further, if the membrane is stained gradually each time of use, carbon dioxide gas becomes hard to flow, so that a deflection occurs in the relation between a carbon dioxide gas pressure and a flow rate created first, thereby disabling a right flow control. Although it may be possible to achieve the right control if the relation between pressure and flow rate is investigated each time of use, the operation for that purpose is very troublesome.

An object of the present invention is to solve the above-described problems and more particularly to provide a device and method for manufacturing carbonated spring and carbonic water having a high concentration effectively, and a device and method for manufacturing carbonated spring and carbonic water capable of always obtaining a constant carbonic acid concentration despite changes in the membrane permeating performance. Another object of the present invention is to provide a membrane module which allows soluble gas to be dissolved into liquid effectively, a method for measuring the concentration of gas dissolved in a solution produced continuously inline and on time, and a device for manufacturing a dissolved solution having a desired gas concentration effectively.

DISCLOSURE OF THE INVENTION

The most basic configuration of the present invention is a device for manufacturing carbonated spring, comprising: a membrane module which dissolves carbon dioxide gas into hot water through a membrane; means for supplying hot water to the membrane module; and means for supplying carbon dioxide gas to the membrane module, wherein a flow control valve which maintains the flow rate of carbon dioxide gas constant is provided between the means for supplying carbon dioxide gas and the membrane module.

Preferably, the flow control valve is a mass-flow-rate type flow control valve, a flow meter is provided between the flow control valve and the means for supplying carbon dioxide gas and further, a pressure control valve for maintaining gas pressure constant is provided between the means for supplying carbon dioxide gas and the flow control valve.

Adopting such configurations enables the flow rate of carbon dioxide gas to be adjusted more accurately.

Further, preferably, the membrane is hollow yarn and the hollow yarn membrane is a three-layered composite hollow yarn membrane in which both sides of a thin nonporous gas permeating layer are sandwiched by porous layers. If adopting the composite hollow yarn membrane, carbon dioxide gas can be dissolved into hot water or water efficiently.

In addition, the second basic configuration of the present invention is a method for manufacturing carbonated spring, wherein, when carbonated spring is manufactured by dissolving carbon dioxide gas into hot water through a membrane, the flow rate of carbon dioxide gas is controlled to be constant. Preferably, as described previously, the carbon dioxide gas flow rate is controlled to be constant by the flow control valve. Preferably, the mass flow rate type flow control valve, a hollow yarn membrane as the membrane and particularly, a three-layered composite hollow yarn membrane in which both sides of a thin nonporous gas permeating layer are sandwiched by porous layers are used. Further, when carbonated spring is manufactured using the circulation type system, the ratio between the flow rate of a circulation pump and the flow rate of carbon dioxide gas is preferred to be in a range of 2 to 20.

Other basic configuration of the present invention is a device for manufacturing carbonated spring comprising: a carbon dioxide gas supply port; a carbon dioxide gas dissolver which communicates with the carbon dioxide gas supply port; a water bath; a circulation pump for feeding water in the water bath into the carbon dioxide gas dissolver and returning the fed water into the water bath; and carbon dioxide gas supply control means for changing the carbon dioxide gas supply velocity during dissolving of carbon dioxide gas Still other basic configuration of the present invention is a method for manufacturing carbonated spring, wherein, when water in a water bath is circulated by a circulation pump through a carbon dioxide gas dissolver while carbon dioxide gas is supplied into the carbon dioxide gas dissolver so as to dissolve carbon dioxide gas into the water bath to raise the carbon dioxide gas concentration of water in the water bath gradually, the carbon dioxide gas supply velocity is retarded in the latter half period of the carbon dioxide gas dissolving time as compared with the former half period thereof. According to this manufacturing method, the carbon dioxide gas concentration of water in the water bath after dissolving of carbon dioxide gas ends is preferred to be 1000 mg/l or more. By setting the carbon dioxide gas concentration to a high concentration, blood circulation in the skin becomes easy to improve due to distal blood vessel expansion action by the contained carbon dioxide gas and increase/expansion of capillary beds by invasion of carbon dioxide gas through the skin.

Still other configuration of the present invention is a device for manufacturing a gas dissolved solution for carbonated spring, comprising: a carbon dioxide gas supply port; a carbon dioxide gas dissolver which communicates with the carbon dioxide gas supply port; a water bath; a circulation pump for feeding water in the water bath into the carbon dioxide gas dissolver and returning the fed water into the water bath; and carbon dioxide gas supply control means for changing the carbon dioxide gas supply velocity during dissolving of carbon dioxide gas.

Preferably, when carbonated spring is manufactured by dissolving carbon dioxide gas into hot water through a membrane, the carbon dioxide gas flow rate is controlled to be constant. Preferably, a mass flow rate type flow control valve is used as the flow control valve, a hollow yarn membrane is used as the membrane, and particularly, a three-layered composite hollow yarn membrane in which both sides of a thin nonporous gas permeating layer are sandwiched by porous layers is used. Further, the latter half of carbon dioxide gas dissolving time is preferred to be longer than the former half of carbon dioxide gas dissolving time. The carbon dioxide gas supply velocity just before dissolving of carbon dioxide gas ends is preferred to be 50% or less with respect to the supply velocity when dissolving of carbon dioxide gas starts. Consequently, carbonated spring having a high concentration can be manufactured effectively.

In order to control the carbon dioxide gas supply velocity, it is permissible to provide plural carbon dioxide gas supply velocity control means in parallel. In this case, the carbon dioxide gas supply velocity control means may be set to different supply velocities and then, changed over in order from the carbon dioxide gas supply velocity control means having the highest setting of the carbon dioxide gas supply velocity. To change over the carbon dioxide gas supply velocity, it is desirable to use an electromagnetic valve and change over in order under electronic control.

Further, to control the carbon dioxide gas supply velocity, preferably, the flow control valve is used.

As described above, the flow control valve is preferred to be a mass flow rate type flow control valve. Preferably, a flow meter is provided between the flow control valve and the means for supplying carbon dioxide gas and a pressure control valve for maintaining gas pressure constant is provided between the means for supplying carbon dioxide gas and the flow control valve. With these structures, the flow rate of carbon dioxide gas can be adjusted accurately.

Generally, as the flow control valve, there are a type affecting the secondary pressure (outlet side pressure) such as an ordinary orifice and needle valve and a type not affecting the secondary pressure. In case of the type affecting the secondary pressure, as the pressure of the secondary side increases, that is, a difference to the primary pressure decreases, the flow rate is reduced. At this time, the valve opening degree (CV value) and pressure are generally in a following relation.

Assuming that $P_1$ is a primary side absolute pressure (MPa), $P_2$ is a secondary side absolute pressure (MPa), Q is a flow rate (m³/h), and $\rho$ is a specific weight (assuming air to be 1), when $P_2 > (P_1/2)$, $$CV = Q/4170 \times (\rho(273+t)/(P_1-P_2)P_2)^{1/2}$$

When $P_2 \leq (P_1/2)$, the secondary pressure is not affected.

On the other hand, the mass flow control valve does not affect the secondary pressure.

According to Japanese Patent Application Laid-Open NO. 58-139730, when the pressure is constant, carbon dioxide gas is fed, that is, because the secondary pressure is constant, the mass flow control valve is not required.

Contrary to this, preferably the mass flow control valve is adopted because the present invention utilizes the membrane module in which the secondary pressure changes depending on changes in state. As a well known mass flow control valve, there are an electronic valve and needle valve. Although according to the present invention, the needle valve type mass flow control valve is preferably used, it is permissible to use the electronic type.

The mass flow control valve of the needle valve type adjusts the flow rate with a needle valve and is provided with a pressure adjusting valve or the like whose opening degree is constant to the same mass flow rate so that the pressure at a valve outlet becomes constant, provided at the rear portion thereof. Consequently, the secondary pressure (outlet pressure) is always kept constant. Because the secondary pressure turns constant when the primary pressure (intake pressure) is constant, the valve is called constant differential pressure adjusting valve. Although the ordinary needle valve affects the secondary pressure, this mass flow control valve can adjust the mass flow rate to constant even if the load pressure on the secondary side (outlet side) changes.

On the other hand, in the electronic mass flow control valve, resistors each having a large resistance temperature coefficient are wound around a capillary tube which is a sensor portion at its upstream and downstream sides and by supplying a current to this, the two resistors are heated. At this time, if no fluid flows through the capillary tube, the upstream and downstream sides are balanced with the same temperature. If fluid begins to flow in this state, the temperature distribution changes, so that the upstream side is deprived of heat by fluid while the downstream side is supplied with heat deprived from the upstream side. That is, there is generated a difference in temperature between the upstream and downstream sides.

If attention is paid to that this temperature difference is in a predetermined functional relationship with the mass flow rate of fluid and a change of each resistance is fetched out as an electric signal and then, amplified and corrected, a thermal type mass flow rate meter capable of measuring the mass flow rate functions under a certain condition. This is an electronic type mass flow rate meter (mass flow meter).

In the mass flow control valve (mass flow controller), a valve opening degree is controlled by a high-speed, high-resolution piezo or solenoid actuator under comparative control with a flow rate setting signal from outside based on a signal of mass flow rate outputted from the sensor portion. Consequently, a stabilized mass flow control is enabled hardly affected by changes in various conditions such as temperature and pressure.

According to the present invention, in the gas permeation membrane preferable for carbon dioxide gas, preferably, its carbon dioxide gas permeating amount at 25° C. is $1 \times 10^{-3}$ to 1 m³/m²·hr·0.1 MPa and its vapor permeating amount at 25° C. is $1 \times 10^3$ g/m²·hr·0.1 MPa or less. Further, it is preferable to use a membrane module composed of these gas permeation membranes. If the gas permeation membrane is a nonporous membrane having no Knudsen flow, the membrane gets wet so that no water permeates to the gas supply side, which is preferable. If the membrane density of the membrane module is in a range of 2000 to 7000 m²/m³, carbon dioxide gas can be dissolved effectively, which is preferable.

It is preferable that the gas permeation membrane is a hollow yarn membrane, because the membrane area per volume can be raised. Although this hollow yarn may be composed of hollow yarn membrane formed of mere porous membrane, if the hollow yarn membrane is a three-layered composite hollow yarn membrane in which both sides of a thin nonporous membrane are sandwiched by porous membranes, carbon dioxide gas can be dissolved into hot water efficiently, which is preferable. If the thickness of the nonporous membrane is 0.1 to 500 μm, an appropriate strength is possessed while carbon dioxide gas permeating performance and vapor permeating performance are satisfied, which is preferable. To dissolve carbon dioxide gas using the carbon dioxide gas adding membrane module, it is preferable to heat water to 30° C. to 50° C. preliminarily and then dissolve it. Further, the carbon dioxide gas dissolver may be a static mixer.

Moreover, to manufacture the above-described high concentration carbonated spring or carbonic water of 1000 mg/l or more, the method for measuring the gas concentration in a dissolved solution which is another aspect of the present invention can be adopted. This is a gas concentration measuring method developed by the inventor of the present invention, and applies the fact that when the flow rate of solution passing the gas dissolver and the supply flow rate of gas supplied to the same gas dissolver are kept constant, there exists a certain correlation between the quantity of bubbles of undissolved gas existing in the take-out pipe from the gas dissolver and the gas concentration in the dissolved solution introduced from the gas dissolver. Consequently, the gas concentration in the dissolved solution manufactured continuously can be measured in line and on time. In the meantime, the gas concentration measuring method of the present invention is not restricted to measurement of the gas concentration in the carbon dioxide gas solution only, but naturally may be applied to measurement of gas concentration of other various kinds of soluble gases.

The basic configuration exists in a method for measuring a gas concentration in a dissolved solution, comprising introducing solution and gas of each specified flow rate into a gas dissolver, measuring the quantity of bubbles existing in a take-out pipe from the gas dissolver and measuring the gas concentration of a dissolved solution discharged from the take-out pipe according to the quantity of the bubbles.

By introducing a specified amount of solution into the gas dissolver and a specified amount of gas, a dissolved solution after gas is dissolved into solution in the gas dissolver and gas not dissolved in solution, that is, gas mixed in the dissolved solution in the form of bubbles is discharged through the take-out pipe from the gas dissolver. The quantity of bubbles of undissolved gas existing in the take-out pipe is measured continuously in line and on time so as to measure the gas concentration in the dissolved solution introduced out from the gas dissolver continuously. As the quantity of gas introduced into the gas dissolver, it is desirable to introduce a quantity not less than the saturated dissolved amount of the quantity of the introduced solution into the gas dissolver.

When obtaining a dissolved solution having a target gas concentration by adding gas to dissolved solution of any concentration through multiple stages, the quantity of gas which can be added in a next stage is decreased as the gas concentration of an initial dissolved solution is higher. Moreover, to maintain the flow rate of solution passing the gas dissolver and the supply flow rate of gas supplied to the same gas dissolver, the quantity of bubbles of undissolved gas existing in the take-out pipe from the gas dissolver and the gas concentration in the dissolved solution introduced out from the gas dissolver have a specific correlation. Using this fact, the gas concentration in the dissolved solution can be measured on time during continuous manufacturing of the dissolved solution by measuring the quantity of bubbles in the dissolved solution in the take-out pipe according to a relational expression, which indicates the relation between the quantity of bubbles in the dissolved solution existing in the take-out pipe and the gas concentration of the dissolved solution and is obtained under various conditions in terms of the dissolving capacity of a gas dissolver, the introduction amount of solution and the flow rate of introduced gas.

When the dissolved solution is artificial carbonated spring, the gas concentration of the artificial carbonated spring manufactured by the gas dissolver can be measured continuously in line and on time effectively from the quantity of bubbles in the take-out pipe during manufacturing of the artificial carbonated spring.

In addition to the above-described configuration, the quantity of the bubbles is preferred to be computed according to the damping rate of ultrasonic wave passing the take-out pipe using an ultrasonic wave transmitter and an ultrasonic wave receiver disposed across the take-out pipe. As regards measuring of bubbles of gas in the dissolved solution, the quantity of bubbles is computed according to a damping rate (=(strength of ultrasonic wave signal received by ultrasonic wave receiver)/(strength of ultrasonic wave signal transmitted from ultrasonic wave transmitter): %) of the strength of an ultrasonic wave signal received by the ultrasonic wave receiver disposed in the take-out pipe after the ultrasonic wave signals dispatched from the ultrasonic wave transmitter disposed in the introduction pipe are passed through the dissolved solution in the take-out pipe.

The quantity of bubbles can be measured by causing the ultrasonic wave signal to pass through the take-out pipe in which the quantity of bubbles of gas in the dissolved solution and the solution coexist. That is, the damping of the ultrasonic wave signal measured by the ultrasonic wave receiver is minimized (the damping rate is maximized) because the ultrasonic wave signal dispatched from the ultrasonic wave transmitter passes only the solution when no gas bubbles exist in the solution (when the supply amount of gas is 0 or gas introduced into the gas dissolver is dissolved 100% in the solution because the gas supply velocity to the flow velocity of the solution is small).

Because the conductivity of ultrasonic wave is different between solution and bubble, the damping of the ultrasonic wave signal increases as more bubbles are mixed in the solution and when the solubility in the gas dissolver for use reaches 0, the damping of the ultrasonic wave signal measured by the ultrasonic wave receiver is maximized (the damping rate is minimized). Because the change in the damping rate of the ultrasonic wave signal is inherent of a gas dissolver, it is possible to obtain a relational expression to a gas dissolver for use by measuring the damping rate of the ultrasonic wave signal and a measured value of the gas concentration in the solution.

Particularly, because when the artificial carbonated spring is adopted as the solution, there is a tendency that the damping rate decreases rapidly from the saturated concentration of carbon dioxide gas in the artificial carbonated spring, the change in the damping rate is large in the vicinity of 1000 to 1400 mg/l which is an effective carbon dioxide gas concentration as the artificial carbonated spring, so that the carbon dioxide gas concentration in the effective carbon dioxide gas concentration range can be measured easily according to the quantity of bubbles.

According to the present invention, preferably, the gas concentration is specified according to the quantity of the measured quantity of bubbles using the relational expression between the quantity of bubbles and gas concentration measured under a condition that the solution flow rate and gas flow rate are constant. Here, the inventor of the present invention has recognized first that there exists a specified correlation between the quantity of bubbles in undissolved gas existing in the take-out pipe from the gas dissolver and the gas concentration in the dissolved solution taken out from the gas dissolver or taken into the gas dissolver by maintaining the flow rate of solution passing the gas dissolver and the supply amount of gas supplied to the same gas dissolver and this recognition is applied to the present invention.

That is, this specification can be carried out according to the relational expression by measuring the damping rate of the ultrasonic wave signal and the measured value of the gas concentration for the state of solution to be introduced to the gas dissolver and the state of gas. The states of the solution and gas can be set up depending on physical condition (for example, flow rate for introduction, pressure, temperature, viscosity and the like). Because the relational expression between the damping rate of the ultrasonic wave signal and the measured value of the gas concentration differs depending on the physical conditions of the solution and gas, it is desirable to keep the above relational expression under a condition for carrying out normal dissolving work.

Because the above-described relational expression differs depending on the dissolving capacity of the gas dissolver, the temperature, pressure and the like at the time of dissolving, it is necessary to set up these conditions depending on the condition for actually manufacturing the dissolved solution to obtain the above relational expression based on the same condition.

Particularly, in case where the artificial carbonated spring is employed as the dissolved solution, it is desirable to obtain the aforementioned relational expression under the condition that the introduction flow rates of the artificial carbonated spring or hot water and the introduction flow rate of carbon dioxide gas are kept at a desired flow rate at a temperature suitable for taking bath as the temperature of hot water of artificial carbonated spring. The gas concentration measuring method of the present invention is capable of obtaining a preferable result if the gas dissolved solution is artificial carbonated spring. In manufacturing, for example, artificial carbonated spring using carbon dioxide gas as its gas, the gas concentration in the artificial carbonated spring being manufactured is measured based on the quantity of bubbles of carbon dioxide gas in the take-out pipe discharged from the gas dissolver.

Thus, the gas concentration of the artificial carbonated spring manufactured by the gas dissolver can be measured continuously on time effectively according to the quantity of bubbles in the take-out pipe during manufacturing of the artificial carbonated spring. Further, by making the bast of a tendency that the damping rate of the ultrasonic wave signal decreases rapidly from the vicinity of the saturated concentration of the carbon dioxide gas of the artificial carbonated spring, the carbon dioxide gas concentration in the vicinity of 1000 to 1400 mg/l, which is an effective carbon dioxide gas concentration as the artificial carbonated spring, can be detected or measured easily.

At a temperature suitable for taking bath in the artificial carbonated spring, an relational expression between the quantity of bubbles of carbon dioxide gas in the artificial carbonated spring taken out from the gas dissolver and the gas concentration of the artificial carbonated spring is obtained preliminarily with the flow rate of the artificial carbonated spring or hot water introduced into the gas dissolver and the introduction flow rate of carbon dioxide gas set to desired specific flow rates. Then, the carbon dioxide gas concentration of the artificial carbonated spring can be obtained in line and on time during manufacturing of the artificial carbonated spring.

According to still another aspect of the present invention, the gas concentration measuring method is achieved by a device for manufacturing a gas dissolved solution, comprising: a gas supply source having gas flow rate adjusting means; a gas dissolver in which gas and solution are to be introduced from the gas supply source; solution flow rate adjusting means for controlling the flow rate of the solution introduced into the gas dissolver to be constant; and a take-out pipe for taking out the solution from the gas dissolver, the manufacturing device further comprising: a measuring device for measuring the quantity of gas bubbles existing in the take-out pipe; and a control device for computing the gas concentration of the dissolved solution based on a relational expression between the quantity of bubbles and gas concentration measured preliminarily under a condition that the solution flow rate and gas flow rate are constant and a measured value from the measuring device and controlling the gas flow rate adjusting means and/or the solution flow rate adjusting means based on the computation result, securely and accurately.

According to the present invention, the gas concentration of a dissolved solution is computed according to the quantity of gas bubbles existing in the take-out pipe under measurement using the relational expression between the quantity of bubbles and gas concentration obtained by preliminary measurement. Then, a dissolved solution having a desired gas concentration can be manufactured by controlling the gas flow rate adjusting means and/or the solution flow rate adjusting means depending on the computed gas concentration of the dissolved solution.

As regards control on the gas flow rate adjusting means and/or the solution flow rate adjusting means, the introduction from the gas flow rate adjusting means and solution flow rate adjusting means into the gas dissolver can be stopped when the gas concentration of the dissolved solution computed by the control device reaches a desired gas concentration. Further, the gas concentration in the dissolved solution can be controlled based on the relational expression at changed flow rates in the gas flow and solution flow.

In this case, a number of the relational expressions between the gas flow rate and solution flow rate, which can be changed over in advance, are prepared preliminarily and then, the gas flow rate and solution flow rate optimum for a desired gas concentration are computed from the gas concentration computed from the quantity of bubbles in the solution. Then, the gas flow rate adjusting means and solution flow rate adjusting means are controlled so as to reach the gas flow rate and solution flow rate on the relational expression which is preliminarily measured and is the nearest the above computation result.

The measuring device is preferred to be composed of the ultrasonic wave transmitter and ultrasonic wave receiver disposed across the take-out pipe. By using the gas dissolved solution manufacturing device having such a configuration, the above-described operation and effect can be obtained.

The gas dissolver may be constituted of a static mixer. Because the static mixer is a gas dissolver capable of introducing a specific amount of solution and soluble gas continuously from viewpoint of its structure and has a relatively high dissolving efficiency, it is advantageous to adopt this as a dissolver. Particularly, because the static mixer is a gas dissolver capable of introducing a specified amount of hot water and carbon dioxide gas continuously and easily upon manufacturing of the artificial carbonated spring and has a high dissolving efficiency for carbon dioxide gas, it is advantageous as a gas dissolver for manufacturing the artificial carbonated spring.

Preferably, the gas dissolver is a hollow yarn membrane type dissolver. The hollow yarn membrane type dissolver allows gas to be dissolved in solution to be supplied at a stable flow rate and secures a high dissolving efficiency, so that gas can be dissolved in solution in a wider concentration range.

In the hollow yarn membrane type dissolver, solution is passed on a contact portion on the surface of the hollow yarn membrane and through one side of the hollow portion while gas is passed through the other side, so that gas is dissolved in solution using the action as a gas exchange membrane in the hollow yarn membrane. At the time of dissolving gas, it is preferable to adjust the gas pressure and solution pressure to a pressure capable of obtaining a dissolved solution not less than the saturated gas concentration by adjusting the gas pressure adjusting unit and solution pressure adjusting unit connected to the hollow yarn membrane type dissolver.

Particularly, its dissolving efficiency is relatively high in a concentration region of 1000 mg/l or more necessary for the artificial carbonated spring for manufacturing of the artificial carbonated spring, the relational expression between the quantity of bubbles and the carbon dioxide gas concentration is maintained excellently and it is capable of detecting the carbon dioxide gas concentration in a carbon dioxide gas concentration region effective for the artificial carbonated spring at a high accuracy.

Preferably, it further comprises a storage bath for storing dissolved solution discharged from the take-out pipe, wherein liquid in the storage bath is circulated to the gas dissolver through the solution flow rate adjusting means. A desired amount of gas can be dissolved in the dissolved solution from the gas dissolver by circulating the solution in the storage bath through the solution flow rate adjusting means. Thus, the dissolved solution in the storage bath is introduced from the storage bath into the gas dissolver through a liquid feeding pump or the like and gas is added gradually to the dissolved solution so as to raise the gas concentration.

By measuring the gas concentration of the dissolved solution passing the gas dissolver, gas can be added until the gas concentration of the dissolve solution in the storage bath reaches a target gas concentration, so that a dissolved solution of a desired gas concentration can be manufactured. At this time, if a relational expression between the damping rate of the ultrasonic wave signal and the gas concentration of the solution introduced into the dissolver instead of the gas concentration of the solution taken out from the dissolver is obtained preliminarily for a gas dissolver for use, the gas concentration of the solution in the storage bath can be detected.

Even if new solution is added to the storage bath, a dissolved solution of a desired gas concentration can be manufactured by circulating the dissolved solution into the gas dissolver. Thus, a dissolved solution of a desired gas concentration can be always held at a specified amount in the storage bath.

On the other hand, a target gas concentration can be manufactured continuously by changing the ratio between the flow rate of solution to be introduced into the gas dissolver and the gas supply flow rate while measuring the gas concentration in the dissolved solution which passes through the gas dissolver, the solution being introduced directly into the storage bath through a supply port such a faucet.

Upon manufacturing of the artificial carbonated spring, the artificial carbonated spring having a desired carbon dioxide gas concentration can be manufactured easily by circulating the artificial carbonated spring to the gas dissolver and further a desired amount of the artificial carbonated spring can be manufactured continuously while measuring the carbon dioxide gas concentration.

BEST MODE FOR CARRYING OUT THE INVENTION

Hereinafter, preferred embodiments of the present invention will be described in detail with reference to the accompanying drawings.

Figure 1:
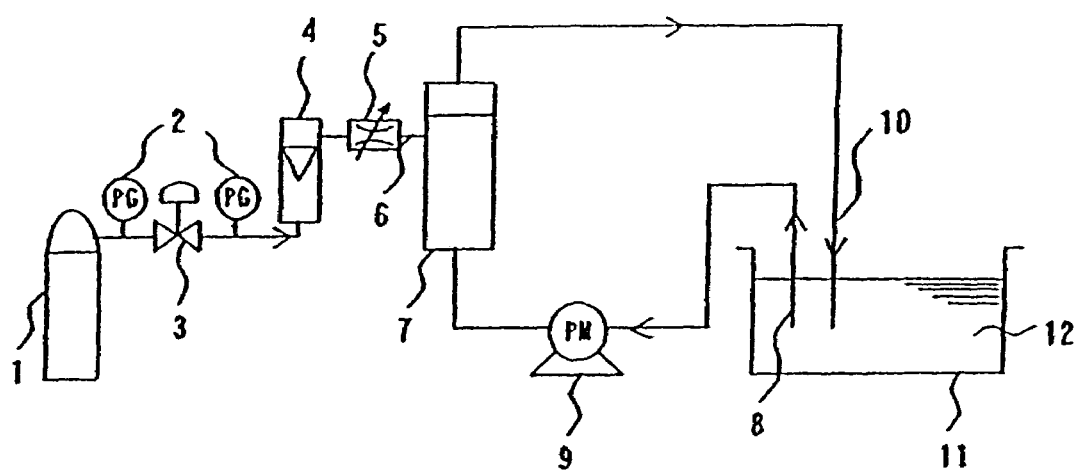
FIG. 1 is a diagram showing a schematic entire configuration of a circulation type device preferably used for the present invention.

FIG. 1 shows a device of circulation type for manufacturing carbonated spring as an example of a diagram schematically showing an entire configuration of a preferable device of the present invention. Reference numeral 1 denotes a carbon dioxide gas cylinder, reference numeral 2 denotes a pressure gauge, reference numeral 3 denotes a pressure control valve, reference numeral 4 denotes a flow meter, reference numeral 5 denotes a flow control valve, reference numeral 6 denotes a carbon dioxide gas introduction intake, reference numeral 7 denotes a carbon dioxide gas dissolver, reference numeral 8 denotes a hot water introduction intake, reference numeral 9 denotes a circulation type suction pump, reference numeral 10 denotes a carbonated spring discharge port, reference numeral 11 denotes a bath and reference numeral 12 denotes hot water.

Figure 2:
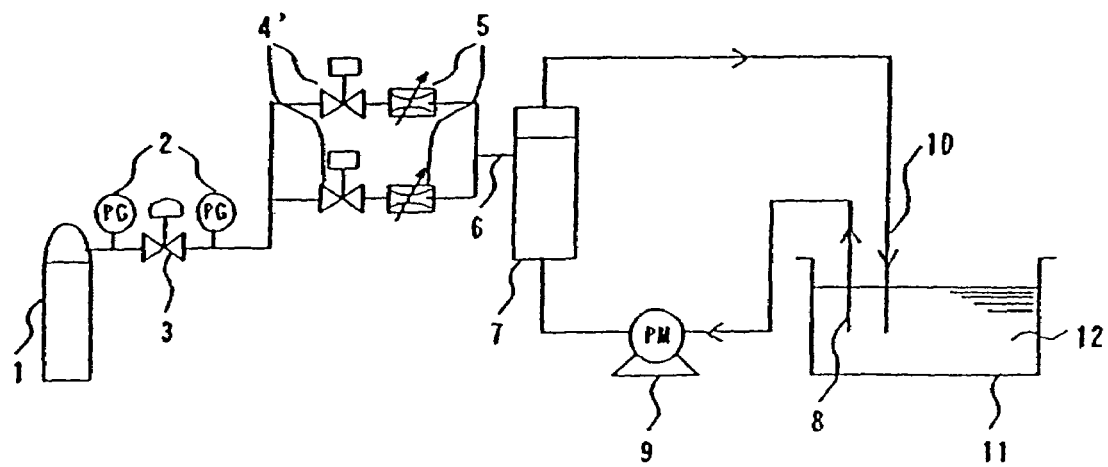
FIG. 2 is a diagram showing a schematic entire configuration of another circulation type device preferably used for the present invention.

FIG. 2 is a diagram schematically showing an entire configuration of another preferred device of the present invention. Reference numeral 1 denotes a carbon dioxide gas cylinder, reference numeral 2 denotes a pressure gauge, reference numeral 3 denotes a pressure control valve, reference numeral 4' denotes an electromagnetic valve, reference numeral 5 denotes a flow control valve, reference numeral 6 denotes a carbon dioxide gas introduction intake, reference numeral 7 denotes a carbon dioxide gas dissolver, reference numeral 8 denotes a hot water introduction intake, reference numeral 9 denotes a circulation type suction pump, reference numeral 10 denotes a carbonated spring discharge port, reference numeral 11 denotes a bath, and reference numeral 12 denotes hot water.

Water in the bath 11 is circulated by the circulation type suction pump 9 through the carbon gas dissolver 7 and carbon dioxide gas is supplied into the carbon dioxide gas dissolver. By dissolving carbon dioxide gas into water (hot water) so as to raise the concentration of carbon dioxide gas in water gradually, carbonated spring of an always high predetermined concentration is produced.

Figure 3:
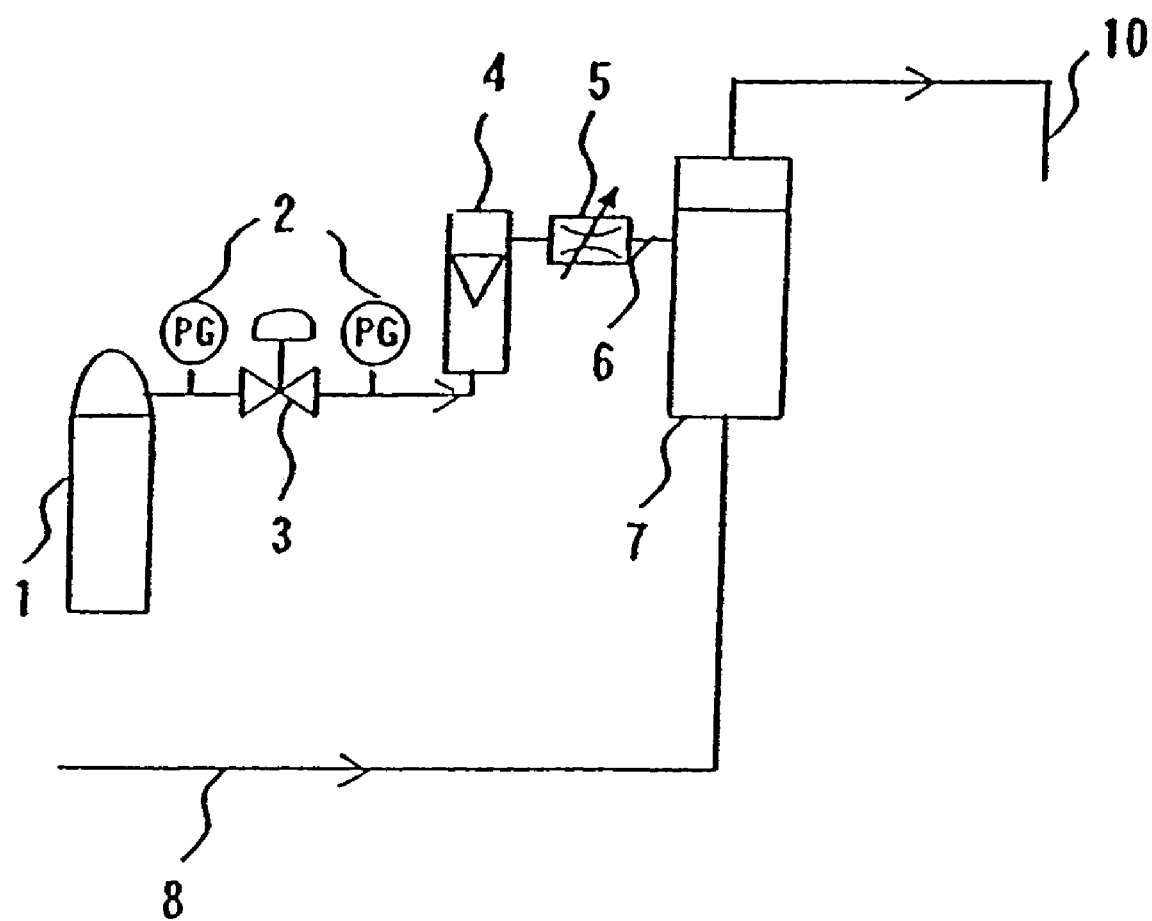
FIG. 3 is a diagram showing a schematic entire configuration of a one-pass type device preferably used for the present invention.

FIG. 3 is a diagram schematically showing an entire configuration of still another preferred device of the present invention, indicating a one-pass type carbonated spring producing device. Reference numeral 1 denotes a carbon dioxide gas cylinder, reference numeral 2 denotes a pressure gauge, reference numeral 3 denotes a pressure control valve, reference numeral 4 denotes a flow meter, reference numeral 5 denotes a flow control valve, reference numeral 6 denotes a carbon dioxide gas introduction intake, reference numeral 7 denotes a carbon dioxide gas dissolver, reference numeral 8 denotes a hot water introduction port and reference numeral 10 denotes a carbonated spring discharge port.

Carbon dioxide gas is reduced to a predetermined pressure from the carbon dioxide gas cylinder 1 by the pressure control valve 3 and the flow rate is controlled by the flow control valve 5. After that, it is fed into the carbon dioxide gas dissolver 7 through which hot water flows so that it is dissolved in the hot water.

Although these devices may be provided with no pressure control valve 3, it is preferable to provide with it for the safety and for control of the flow control valve 5, which is provided later. Although the pressure control valve 3 is not restricted to any particular type, an ordinary pressure reduction valve, whish is installed directly on a cylinder, may be accepted.

Pressure control of carbon dioxide gas applied on the membrane is not required and what is important is control on the flow rate of carbon dioxide gas flowing on the membrane. If the flow rate of the carbon dioxide gas is regulated to constant, pressure applied on the membrane is high in the initial period of gas passage and thereafter, it drops gradually. The membrane is stained each time when it is used, so that the pressure rises gradually, but the pressure of carbon dioxide gas applied to the membrane does not affect manufacturing of carbonated spring at a high precision.

Thus, flow control on the carbon dioxide gas flowing on the membrane is very important. As the flow control valve 3, various kinds of needle valves, for example, electronically used piezo or solenoid actuator can be picked up and although not particularly limited, a needle valve is preferable because it is cheap. Further, it is permissible to use an orifice having a throttle. The function of this flow control valve 5 is important for the present invention and particularly, even if the pressure or temperature changes, a mass flow rate type which has the function for always keeping the flow rate constant is preferable. A pressure is applied when carbon dioxide gas is fed into the carbon gas dissolver and the pressure differs between in the initial period of gas passage and at the stabilizing time. Thus, a type having this function can perform more stabilized flow control.

Although the flow control valve 5 can always control the flow rate to constant if its knob is fixed, it is preferable to provide with a flow meter because the flow meter can be checked visually and judged instantly when any trouble occurs. As the flow meter, a float type volume flow meter and current temperature difference detection type mass flow meter can be mentioned and although not limited, the mass flow meter is more unlikely to be affected by the pressure and temperature.

Regarding the flow rate of carbon dioxide gas, in case of the circulation type, the flow rate ratio between the flow rate of the circulation pump and carbon dioxide gas is set to 2 to 20, preferably, 3 to 10. Within this range, the dissolving efficiency is raised. If it is smaller than that range, the dissolving efficiency drops remarkably and conversely if it is larger, the dissolving efficiency is excellent but the flow rate of the circulation pump is increased or the flow rate of carbon dioxide gas is decreased. Thus, consumption power is consumed wastefully or the production time is prolonged, which is not preferable. In case of one-pass type, the flow rate of carbon dioxide gas per unit membrane area is set to be in a constant range.

As the carbon gas dissolver, a membrane module can be used.

Although as the configuration of the membrane in the carbon gas dissolver, flat membrane, tubular membrane, hollow yarn membrane, spiral membrane and the like can be mentioned, the hollow yarn membrane is most preferable in terms of compactness of the device and ease of handling.

Various kinds of membranes may be used as long as they have an excellent gas permeability, and both porous hollow yarn membrane and nonporous hollow yarn membrane are acceptable. If the porous hollow yarn membrane is used, the diameter of an opening hole in its surface is preferred to be 0.01 to 10 $\mu$m. The most preferable hollow yarn membrane is a three-layer composite hollow yarn membrane in which a thin nonporous gas permeable layer is sandwiched by porous layers on both sides and its specific example is, for example, a three-layer composite hollow yarn membrane (MHT-200TL, product name) made by Mitsubishi Rayon Co., Ltd.

The nonporous gas permeable layer (membrane) is a membrane which gas passes by a dissolving/diffusion mechanism to its membrane substrate and any membrane is acceptable if molecules substantially do not contain holes which gas can pass in a gas form like Knudsen flow. If the nonporous substance is used, the gas can be supplied and dissolved without being emitted into carbonated spring as bubbles under any flow rate thereof and further dissolved effectively and controlled to any concentration because it can be dissolved easily. Although in case of the porous membrane, hot water sometimes backflows to the gas supply side through pores, in case of the nonporous membrane, no hot water backflows to the gas supply side through the pores. In the three-layer composite hollow yarn membrane, its nonporous layer is formed very thinly to have an excellent gas permeability and protected by porous substance so that it is hard to damage.

The gas permeation membrane is preferred to be of nonporous membrane including no Knudsen flow, thereby there being no fear that the membrane turns hydrophilic during a long term usage, causing a water leakage.

As described above, the membrane thickness of the nonporous membrane is preferred to be in a range of 0.1 $\mu$m to 500 $\mu$m. If the membrane thickness is smaller than 0.1 $\mu$m, the membrane production and handling are difficult. If the membrane thickness is larger than 500 $\mu$m, the vapor permeating amount drops while the carbon gas permeating amount drops also, so that a very large membrane area is required to obtain a necessary performance.

Preferably, the membrane thickness of the hollow yarn membrane is 10 to 150 $\mu$m. If it is less than 10 $\mu$m, membrane strength becomes insufficient and if it exceeds 150 $\mu$m, the passing velocity of carbon dioxide gas drops so that its diffusion efficiency is likely to drop. In case of the three-layer composite hollow yarn membrane, the thickness of the nonporous membrane is 0.3 to 20 $\mu$m. If it is less than 0.3 $\mu$m, membrane deterioration is likely to occur and if the membrane is deteriorated, leakage is likely to occur. If the membrane thickness exceeds 20 $\mu$m, the passing velocity of carbon dioxide gas drops, which is not preferable.

Examples of a preferable hollow yarn membrane material include silicone base, polyolefin base, polyester base, polyamide base, polyimide base, polysulfone base, cellulose base, polyurethane base and the like. Examples of the preferable materials of the nonporous membrane in the three-layered composite hollow yarn membrane include polyurethane, polyethylene, polypropylene, poly-4-methylpentene-1, polydimethylsiloxane, polyethyl cellulose, polyphenylene oxide and the like. Particularly, polyurethane has an excellent membrane producing property with a small amount of eluted substance.

If the hollow yarn membrane is used for the carbon dioxide gas dissolver, there are a method in which carbon dioxide gas is supplied inside pores in the hollow yarn membrane and hot water is supplied to the side of the outer surface so as to dissolve carbon dioxide gas and a method in which carbon dioxide gas is supplied to the side of the outer surface of the hollow yarn membrane and hot water is supplied inside pores so as to dissolve carbon dioxide gas. If carbon dioxide gas is supplied to the outer surface of the hollow yarn membrane while hot water is supplied inside the pores so as to dissolve carbon dioxide gas, carbon dioxide gas can be dissolved in hot water at a high concentration regardless of the configuration of the membrane module.

The inside diameter of the hollow yarn membrane is preferred to be 50 to 1000 μm. If it is less than 50 μm, resistance of a flow path to carbon dioxide gas or hot water flowing through the hollow yarn membrane is increased, so that supply of carbon dioxide gas or hot water is disabled. Further, if it exceeds 1000 μm, the size of the dissolver is increased, thereby not making it possible to achieve compactness thereof.

In the carbon dioxide gas dissolver for use in the present invention, the gas diffusing portion composed of porous substance may be provided with gas diffusing means installed on the bottom portion of the carbon dioxide gas dissolver. Although the material and configuration of the porous substance disposed in the gas diffusing portion are not restricted to any particular ones, porosity, namely, volume ratio to the entire porous substance of pores existing in the porous substance itself is preferred to be in a range of 5 to 70 vol %. To raise the dissolving efficiency of carbon dioxide gas, it is better as the porosity is lower and it is preferred to be 5 to 40 vol %. If the porosity exceeds 70 vol %, it is difficult to control the flow rate of carbon dioxide gas so that bubbles of carbon dioxide gas diffused from the porous substance become huge thereby likely decreasing the diffusing efficiency. If the porosity is less than 5 vol %, the supply amount of carbon dioxide gas decreases and thus, it tends to take a long time to dissolve carbon dioxide gas.

Figure 4:
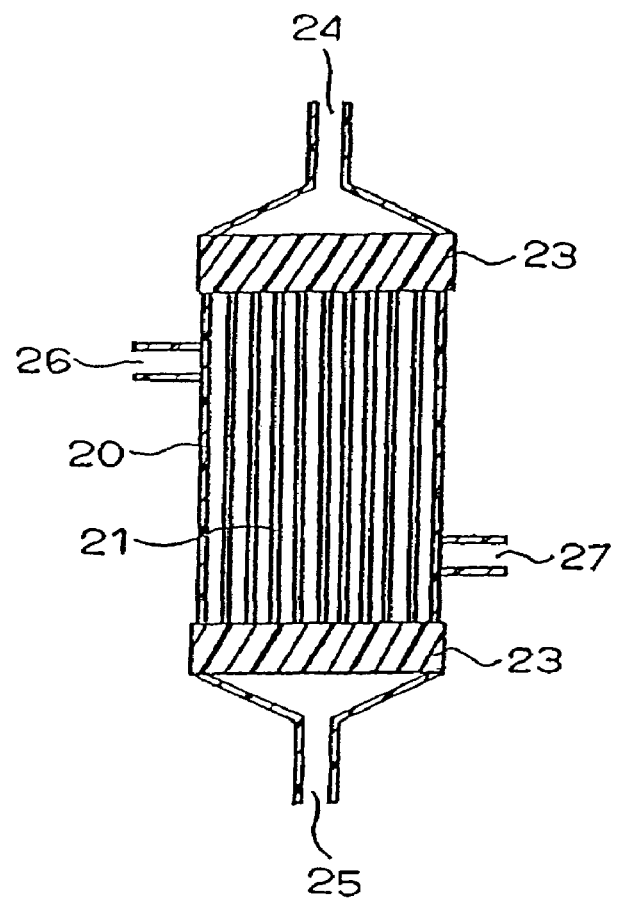
FIG. 4 is a schematic sectional view showing an example of a carbon dioxide gas adding membrane module of the present invention.

FIG. 4 is a sectional view showing an example of the hollow yarn membrane module of the present invention. A hollow yarn membrane 21 is fixed to a fixing member 23 within a housing 20 with opening state at both ends thereof kept and the side in which water flows and the side in which carbon dioxide gas is supplied are sealed by the fixing member 23 such that no liquid is permitted to enter.

The housing 20 is provided with an intake 24 and an outlet 25 communicating with a hollow portion in the hollow yarn membrane 21. Further, it is provided with an intake 26 and an outlet 27 communicating with the outer surface of the hollow yarn membrane 21.

As the gas permeation membrane used in the present invention, a membrane whose carbon dioxide gas permeating amount at 25° C. is $1 \times 10^{-3}$ to 1 $m^3/m^2 \cdot hr \cdot 0.1$ MPa is used. If the carbon dioxide gas permeating amount is lower than $1 \times 10^{-3}$ $m^3/m^2 \cdot hr \cdot 0.1$ MPa, carbon dioxide gas cannot be dissolved in water efficiently and if it is higher than 1 $m^3/m^2 \cdot hr \cdot 0.1$ MPa, a large amount of carbon dioxide gas permeates under a low pressure. Thus, even a small deflection in pressure is not preferable because the permeating amount changes largely.

Further, the gas permeation membrane for use is a membrane whose vapor permeating amount at 25° C. is $1 \times 10^3$ $g/m^2 \cdot hr \cdot 0.1$ MPa or less. If the vapor permeating amount is higher than $1 \times 10^3$ $g/m^2 \cdot hr \cdot 0.1$ MPa, a necessity of discharging drain out of the membrane module frequently occurs, which is not preferable.

Furthermore, if the carbon dioxide gas permeating amount is $1 \times 10^{-2}$ to $1 \times 10^{-1}$ $m^3/m^2 \cdot hr \cdot 0.1$ MPa and the vapor permeating amount is $1 \times 10^{-2}$ $g/m^2 \cdot hr \cdot 0.1$ MPa or less, it is more preferable.

The vapor permeating amount and carbon dioxide gas permeating amount mentioned here refer to weight of vapor and volume of the carbon gas permeation membrane per unit area and unit time when differential pressure of 0.1 MPa is applied between membranes at the ambient temperature of 25° C.

If the carbon dioxide gas permeating amount is high in case of the membrane used for dissolving carbon dioxide gas conventionally, the vapor permeating amount is also high. Thus, if drain is discharged out of the membrane module frequently, the dissolving efficiency of carbon dioxide gas cannot be maintained, and particularly in case of hot water, this problem is remarkable.

The configuration of the membrane is not restricted to any particular one but it may be formed into a desired configuration, for example, hollow yarn membrane configuration, flat membrane configuration and other configurations as required. However, the hollow yarn membrane configuration is preferable because the membrane area per volume of the module can be increased when it is processed to the module.

Although the membrane can be formed of only the nonporous membrane for the reason for the stiffness and thickness of the material of the gas permeation membrane, if the membrane thickness is minute or it is, for example, of flat membrane in order to protect the membrane surface, it is permissible to use a reinforcement porous substance as a spacer. If it is formed of the hollow yarn membrane, it is possible to form to a multi-layer membrane by providing a supporting layer for supporting the hollow yarn membrane on the inner surface and/or the outer surface. These methods may be selected appropriately.

Figure 5:
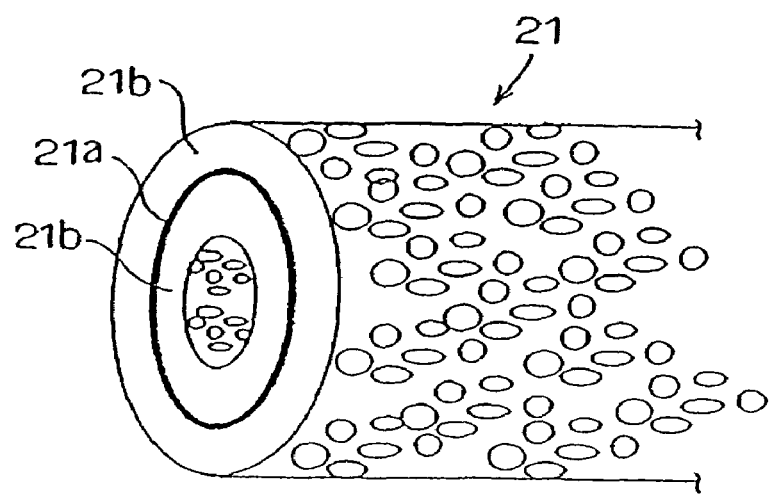
FIG. 5 is a schematic view showing an example of a hollow yarn membrane for use in the present invention.

FIG. 5 shows an example of the desirable configuration of the membrane used for the present invention, which is a composite hollow yarn membrane 21 comprised of three layers while having porous layers 21b on both sides of a nonporous layer 21a. Because in such a composite hollow yarn membrane 21, both faces of the gas permeating nonporous membrane 21a are protected by the porous membrane 21b, the nonporous layer is not directly touched at the time of processing or handling for actual usage, so as to protect the membrane from damage or contamination and further, the obtained hollow yarn membrane has an excellent mechanical strength also.

Examples of a gas permeating nonporous membrane material include a nonporous membrane composed of segmented polyurethane or polymer blend of styrene base thermoplastic elastomer and polyolefin. More specifically, (S)-(EB)-(S) tri-block copolymer composed of copolymer (EB) produced by styrene base thermoplastic elastomer's hydrogenating styrene copolymer (S) and butadiene copolymer, nonporous membrane, which is (S)-(BU)-(S) tri-block copolymer composed of styrene copolymer (S) and butadiene copolymer (BU), polymer produced by hydrogenating random copolymer composed of styrene monomer and butadiene monomer, random copolymer composed of styrene monomer and butadiene monomer and the like can be mentioned.

As for the composition ratio of styrene base thermoplastic elastomer and polyolefin, it is preferable that styrene base thermoplastic elastomer is 20 to 95 mass portion and polyolefin is 80 to 5 mass portion with respect to 100 mass portion which is total of both the compositions and more preferably, the styrene base thermoplastic elastomer is 40 to 90 mass portion while the polyolefin is 60 to 10 mass portion.

When the composite hollow yarn membrane is used, as a polymer material which constitutes a porous layer, it is permissible to use polyethylene, polypropylene, polyolefin base polymer such as poly(3-methylebutene-1) and poly(4-methylpentene-1), polyvinylidene fluoride, fluoro base polymer such as polytetrafluorethylene, polystyrene, and polymer such as polyether ether keton and polyether keton.

As regards the membrane forming method, an appropriate known membrane forming method may be selected depending on the formability, moldability and the like of the material. If taking an example of forming a hollow yarn membrane configuration, a material of a carbon dioxide gas adding membrane is extruded in a molten state from a hollow pipe sleeve and after cooling, wound up according to a conventionally well known method.

To dissolve carbon dioxide gas into water, water is fed to one surface of the gas permeation membrane and carbon dioxide gas is applied with a pressure to the other surface thereof. If the hollow yarn membrane is used, it is permissible to adopt a method in which water is fed into the hollow portion in the hollow yarn membrane while carbon dioxide gas is applied to the outside of the hollow yarn membrane (hereinafter called internal circulation method) or it is permissible to adopt a method in which liquid is fed outside the hollow yarn membrane while carbon dioxide gas is applied to the hollow portion (hereinafter, called external circulation method). Any one of these methods may be used.

If the hollow yarn membrane module 20 having the structure shown in FIG. 4 is used, in case of the internal circulation method, water is supplied to the hollow portion in the hollow yarn membrane 21 from the intake 24 and further, carbon dioxide gas is supplied under an appropriate pressure to the outside of the hollow yarn membrane 21 from the intake 26. Consequently, water in which carbon dioxide gas is dissolved can be obtained from the outlet 25. The outlet 27 is usually closed at this time and opened as a drain discharge port if necessary to discharge water which permeates as vapor.

In case of the external circulation method, carbon dioxide gas is supplied into the hollow portion in the hollow yarn membrane 21 from the intake 24 and water is supplied to the outside of the hollow yarn membrane 21 from the intake 26 and then, water in which carbon dioxide gas is dissolved is obtained from the outlet 27. At this time, usually, the outlet 25 is closed and then opened as a drain discharge port appropriately to discharge water which permeates as vapor.

The drain discharge port is preferred to be disposed at a position which allows drain collected in a space on the side of the carbon dioxide gas in the hollow yarn membrane module to be discharge without any remaining and provided at a position located on the bottom when a module is provided.

In some case, the drain discharge port is provided with an opening/closing valve which is closed when carbon dioxide gas is added and opened/closed manually as required. In other case, it is provided with an electromagnetic valve, which is opened or closed every specified time or may be automatically opened when a predetermined amount of drain is collected by a water level sensor or the like which is installed in a space on the gas side.

As for the discharge of drain, after the supply of carbon dioxide gas is stopped, water can be discharged using a remaining pressure of carbon dioxide gas remaining in the membrane module. If the drain is discharged too frequently at this time, the amount of carbon dioxide which is discharged out of the module together with the drain and consumed without being dissolved in water is increased. Thus, it is economically important to use a membrane having a low vapor permeability to avoid the drain discharge if possible.

Particularly, in case of the external circulation method, drain is collected inside the hollow yarn membrane and the volume in which drain is deposited is smaller than the internal circulation method. Thus, the permeating vapor amount is small and therefore, using a membrane generating not so much drain is very effective.

Preferably, the membrane density inside the carbon dioxide gas adding membrane module is set in a range of 2000 to 7000 $m^2/m^3$ in order to allow carbon dioxide gas or water contact the membrane surface effectively and keep water feeding pressure loss in an appropriate range.

Further, the internal circulation method has such an effect that drain is moved to the bottom of the module without any remaining by its weight and discharged in a short time in addition to an effect that carbon dioxide gas can be dissolved efficiently by keeping the membrane density in this range.

More preferably, the membrane density is in a range of 4000 to 6000 $m^2/m^3$.

The membrane density of the membrane module refers to a value obtained by dividing the membrane area of the membrane module by the volume of the membrane module. In the meantime, the membrane area of the membrane module refers to the total area of the membrane surface, which is a larger one of the side in contact with liquid or the side in which gas is supplied. In case of the composite hollow yarn membrane having three layers in which the porous layers are disposed on both sides of the aforementioned nonporous layer, it refers to a sum of the outside surface area of the porous layer.

The volume of the membrane module refers to the volume of a space in which the hollow yarn membrane 21 is disposed excluding connection portions for suction or liquid feeding in case of the membrane module integrated with the housing 20. In case of a type which is accommodated in a cylindrical housing 20 having plural slits like an ordinary 10-inch cartridge, it refers to the volume of a space in which the hollow yarn membrane 21 is disposed within the cylindrical housing.

It is described that there exists a blood flow rate increase effect when carbon dioxide gas concentration exceeds about 300 mg/l as described in "The effects of external $CO_2$ application on human skin microcirculation investigated by laser Doppler flowmetry. Int J Microcirc: Clin Exp 4:343-350 (1985)" and the carbon dioxide gas concentration is preferred to be 300 mg/l or more.

On the other hand, the saturated solubility of carbon dioxide gas at 40° C. is about 1300 mg/l, and even if more carbon dioxide gas than this concentration is added, the dissolving efficiency drops so that undissolved gas is spouted from the outlet together with water, which is not preferable.

As for the method for adjusting a carbon dioxide gas concentration, it can be adjusted easily by adjusting the supply pressure of carbon dioxide gas with such a pressure adjusting unit as a regulator.

If water temperature is raised after gas is added, dissolved gas returns to bubbles so that the gas concentration in water drops, which is not preferable. Thus, the temperature of water flowing the water path is preferred to be adjusted in a range of 30° C. to 50° C.

If the water temperature is 30° C. or higher, generally, discomfort is not felt when the skin makes contact with the water in foot bathing or taking shower. If water is not used just after carbon dioxide gas is added, it is permissible to add carbon dioxide gas at temperatures about 50° C. and adjust the water temperature to a suitable one by allowing it to cool. A preferable temperature range is from 35° C. which is a temperature around the human temperature to 40° C.

Because the vapor permeating amount increases as the temperature increases, the carbon dioxide gas adding module of the present invention can be used preferably when carbon dioxide gas is dissolved into hot water.

The diameter of an opening in the surface of the porous substance is preferred to be 0.01 to 10 μm in order to control the flow rate of diffused carbon dioxide gas and form minute bubbles. If the hole diameter exceeds 10 μm, bubbles rising in water become too large, thereby the dissolving efficiency of carbon dioxide gas being likely to drop. Further, if it is less than 0.01 μm, the diffused amount in water decreases so that carbonated spring having a high concentration is likely to be impossible to obtain.

The porous substance disposed in the diffusing portion of the diffusing means is capable of generating more bubbles as the surface area thereof is larger, so that contact between carbon dioxide gas and hot water is progressed efficiently and further, dissolving before generation of the bubbles is progressed, thereby intensifying the dissolving efficiency. Therefore, although the configuration of the porous substance is not restricted to any particular one, it is more preferable as the surface area is larger. Although as means for enlarging the surface area, there are various methods, for example, a method of forming the porous substance cylindrically and a method of forming a flat shape and providing its surface with unevenness, it is preferable to use the porous hollow yarn membrane and particularly, using a bundle of multiple porous hollow yarn membranes is effective.

As the material of the porous substance, various kinds of materials, such as metal, ceramic and plastic can be mentioned. Hydrophilic material is not preferable because hot water invades into the diffusing means through pores in the surface when the supply of carbon dioxide gas is stopped.

Although the temperature of hot water for use is not restricted, preferably, it is from 30 to 45° C. and more preferably, it is 35 to 40° C. because the highest heat insulation effect is secured.

Some types of instruments for measuring the concentration of carbon dioxide gas dissolved in water have been well known. A circulation type carbon dioxide gas concentration meter comprises a carbon dioxide gas electrode and a carbon dioxide gas concentration indicator. Electrode membrane and internal liquid need to be replaced every one to three months, so that its maintenance takes time and labor and the cost is high. Further, because it is disadvantageous for measurement of a high concentration, it lacks practical performance as a measuring instrument for use in the device for manufacturing carbonated spring.

A thermal conductivity detection type carbon dioxide gas concentration meter used in a carbonic beverage manufacturing device is very expensive and not suitable for measurement of the concentration of carbonated spring. As a low cost method, there is a method of calculating according to alkaline degree and pH of raw water used for carbonated spring. Carbon dioxide gas concentration in carbonated spring and pH of carbonated spring have a specified relation and the relation between the carbon dioxide gas concentration and pH of carbonated spring changes depending on the alkaline degree of raw water. Thus, to obtain the carbonic acid concentration from pH, the alkaline degree of the raw water needs to be measured. However, if this is obtained, the carbon dioxide gas concentration can be measured easily from pH. Generally, the relation among alkaline degree, pH and carbon dioxide gas concentration is established by a following Tillman's expression.

$$\text{Carbon dioxide gas concentration (mg/l)}= 10^{log[alkaline\ degree(CaCo_3mg/l)]+6.31-pH}$$

Generally, the alkaline degree of raw water is not changed so much with a time passage if that is water obtained from a certain water source such as tap water. Thus, if a carbonated spring manufacturing device is installed and the alkaline degree of raw water is measured before this is started, the value can be used after that. Of course, the alkaline degree of raw water may be obtained each time when the carbonated spring manufacturing device is used. In the meantime, the alkaline degree mentioned here is a way for indicating the amount of content of component which consumes acid such as OH, $CO_3^{2-}$, $HCO_3$ and the like contained in raw water and it is preferable to adopt pH 4.8 alkaline degree (M alkaline degree). For this method, pH needs to be analyzed at a high precision and its error needs to be suppressed within ±0.5 and more preferably, within ±0.01. Therefore, it is preferable to calibrate periodically, preferably each day of usage.

As another style of the carbon dioxide gas dissolver, a static mixer can be mentioned. The static mixer is for separating fluid mechanically to diffuse carbon dioxide gas and not clogged in terms of its structure even if a foreign matter is mixed in fluid so that it can be used for long hours. The detail of the static mixer is described in Chapter 1 of, for example, Basic and Application of Static Mixer, supervised by Shingo Hagiwara, issued by Nikkan Kogyo Shinbunsha (first edition is published Sep. 30, 1981).

Although the solubility of carbon dioxide gas differs depending on the performance of the dissolver, in case of circulation type, it is determined depending on the supply velocity of water supplied to the carbon dioxide gas dissolver, namely, the ratio between the flow rate of the circulation pump and the supply velocity of carbon dioxide gas supplied to the dissolver. The lower the ratio between the carbon dioxide gas supply velocity and water supply velocity, the higher the solubility is. If the water supply velocity is constant, the carbon dioxide gas supply velocity needs to be reduced to reduce the ratio between the carbon dioxide gas supply velocity and the water supply velocity. In this case, there is a disadvantage that manufacturing time is prolonged. However, the relation between the ratio between the carbon dioxide gas supply velocity and water supply velocity and the solubility differs depending on the concentration of carbon dioxide gas in water circulated to the dissolver. As the concentration is lower, the solubility keeps excellent even if the ratio between the carbon dioxide gas supply velocity and water supply velocity is low and as the concentration is increased, the solubility drops unless the ratio between the carbon dioxide gas supply velocity and water supply velocity is increased. According to a prior art, carbon dioxide gas is supplied at the same supply velocity from a manufacturing startup to the end thereof without considering such a matter and by changing the carbon dioxide gas supply velocity halfway, carbonated spring can be manufactured at an excellent solubility.

For example, the carbon dioxide gas supply velocity at a startup of manufacturing is increased and when 10 to 50% the manufacturing time is passed, the supply velocity of the carbon dioxide gas is reduce to about ½ to ⅒. By executing this operation, it is possible to improved the solubility and reduce the consumption of the carbon dioxide gas without prolonging the manufacturing time. This is just an example and the carbon dioxide gas supply velocity can be changed through multi-stages.

To change the carbon dioxide gas supply velocity halfway in this way, plural carbon dioxide gas supply velocity means are provided in parallel as shown in FIG. 2 and in front half of the manufacturing time, an electromagnetic valve 4' for which the carbon dioxide gas supply velocity is set fast by the flow control valve 5 is opened in order to accelerate the carbon dioxide gas supply velocity while the other valve is closed. In rear half of the manufacturing time, an electromagnetic valve 4' for which the carbon dioxide gas supply velocity is set slow is opened in order to retard the carbon dioxide gas supply velocity while the other valve is closed. Although two flow control valves 5 are used here, it is permissible to control with three or more flow control valves.

In this indicated example, the circulation pump 9 is necessary for manufacturing carbonated spring in the circulation system. As the pump, a volume type proportioning pump having a self suction performance is preferable. Using this enables stabilized circulation and always constant circulating water quantity to be achieved. Although if the carbonated spring is dense, bubbles are more likely to occur so that a bubble rich state is generated, even in this case, stabilized water feeding is achieved if a pump having self suction performance which can be started without priming at the initial operation time is used.

In case where artificial carbonated spring is manufactured continuously, the artificial carbonated spring having a predetermined carbon dioxide gas concentration can be manufactured by combining the means for measuring the carbon dioxide gas concentration and the method of manufacturing the artificial carbonated spring. As the method for measuring the concentration of carbon dioxide gas in water, measurement based on the ion electrode system is a general method. However, measurement in line and on time is impossible because it takes a long time until the ion electrode is balanced in a solution having a high concentration required by the artificial carbonated spring and an accurate measurement is impossible as gas bubbles adhere to the ion electrode.

Hereinafter, a carbonated spring continuous manufacturing device equipped with the carbon dioxide gas concentration measuring device of a typical embodiment of the present invention will be described with reference to the accompanying drawings. According to this embodiment, the example of the artificial carbonated spring will be described. The gas concentration measuring method and gas dissolved solution manufacturing device of the present invention are not restricted to the artificial carbonated spring but may be applied to gas concentration measurement of any solution obtained by dissolving gas regardless of the kind of the gas.

Figure 6:
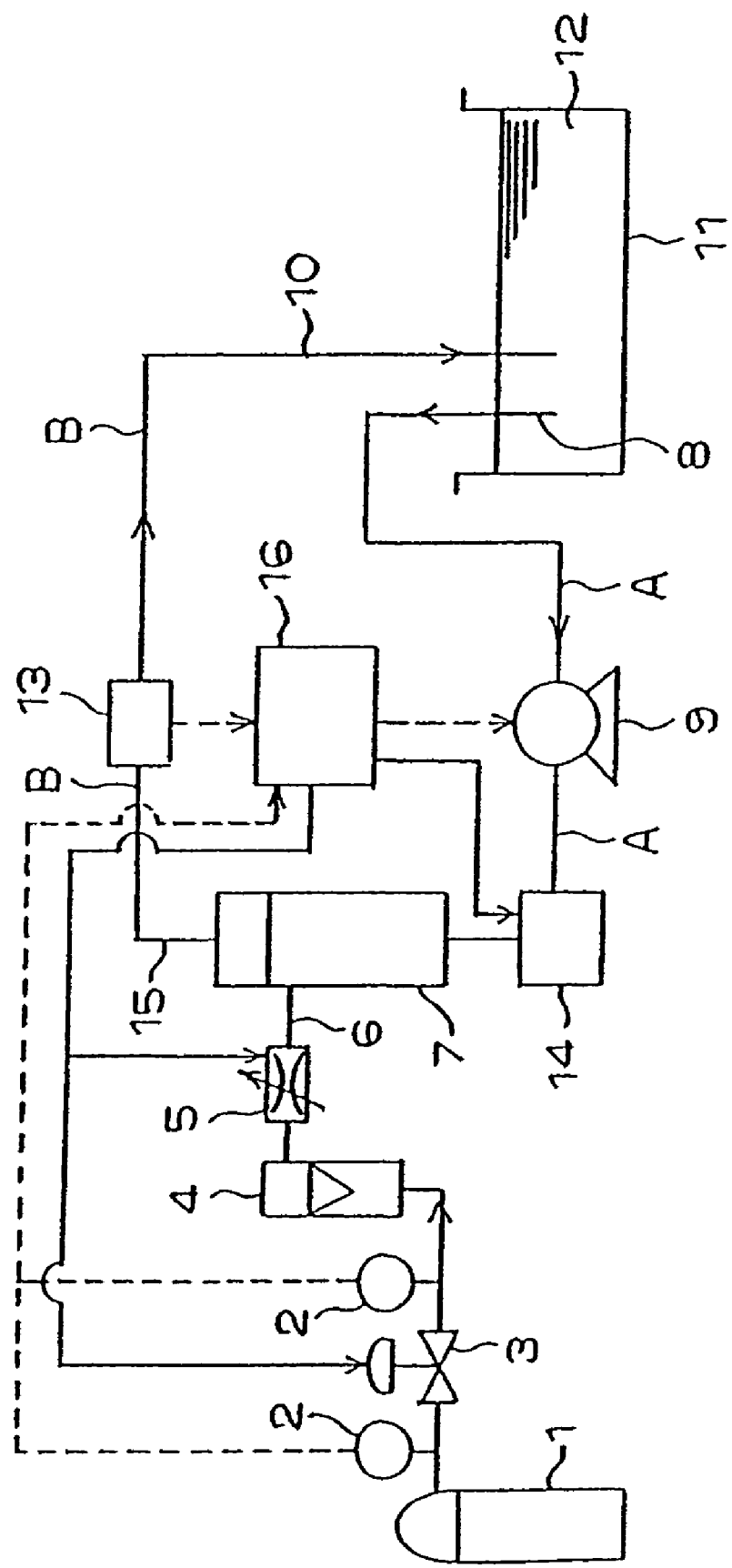
FIG. 6 is a diagram showing a configuration of a device for manufacturing artificial carbonated spring according to an embodiment of the present invention.

FIG. 6 is a diagram showing a configuration of the artificial carbonated spring manufacturing device of the present invention.

As shown in the same figure, a take-in pipe A and a return pipe B for circulating hot water 12 (after carbon dioxide gas is dissolved, turns to artificial carbonated spring) loaded in the bath 11 as a storage bath for the artificial carbonated spring communicate with the inside of the bath. Part of the return pipe B is constituted as a take-out pipe 15 from the carbon dioxide gas dissolver 7. The hot water 12 in the bath 11 is pumped up through the take-in pipe A by the suction pump 9 and a predetermined amount of the hot water 12 is introduced into the carbon dioxide gas dissolver 7 as a gas dissolver through solution flow rate adjusting means 14.

Carbon dioxide gas supplied from the carbon dioxide gas cylinder 1 is adjusted in pressure by the pressure adjusting means 3 and the carbon dioxide gas discharged from the pressure adjusting means 3 is adjusted in terms of the flow rate by the gas flow rate adjusting means 5 and then introduced into the carbon dioxide gas dissolver 7. Detection values detected by the pressure gauges 2 provided before and after the pressure adjusting means 3 are inputted to the control device 16 and then, the pressure adjusting means 3 is controlled by a control signal from the same control device 16 so as to adjust the pressure of the carbon dioxide gas.

Artificial carbonated spring discharged from the carbon dioxide gas dissolver 7 through the take-out pipe 15 and containing bubbles is subjected to measurement about the quantity of bubbles of carbon dioxide gas in the take-out pipe 15 by a measuring device 13 and returned into the bath 11 through the artificial carbonated spring discharge port 10.

The measuring device 13 is provided with an ultrasonic wave transmitter and an ultrasonic wave receiver disposed across the take-out pipe 15 and ultrasonic wave dispatched from the ultrasonic wave transmitter is received by the ultrasonic wave receiver so as to measure the strength of the received ultrasonic wave. A measurement value obtained by the measuring device 13 is inputted to the control device 16.

The control device 16 computes the carbon dioxide gas concentration in the artificial carbonated spring discharged into the take-out pipe 15 according to a relational expression between the quantity of bubbles in carbon dioxide gas preliminarily measured (damping rate of ultrasonic wave received by ultrasonic wave receiver=(strength of ultrasonic wave signal received by ultrasonic wave receiver) (strength of ultrasonic wave signal dispatched from ultrasonic wave transmitter): measured in terms of %) and a measured value of the carbon dioxide gas concentration in the artificial carbonated spring discharged from the carbon dioxide gas dissolver 7, corresponding to the flow rate of the hot water 12 introduced into the carbon dioxide gas dissolver 7 and the introduction amount of carbon dioxide gas.

Corresponding to the carbon dioxide gas concentration of the artificial carbonated spring by the control device 16, the solution flow rate adjusting means 14, the suction pump 9, the gas flow rate adjusting means 5 and the pressure adjusting means 3 are controlled so as to adjust the carbon dioxide gas concentration of the artificial carbonated spring discharged from the carbon dioxide gas dissolver 7. When the carbon dioxide gas concentration of the same artificial carbonated spring reaches a desired carbon dioxide gas concentration, the suction pump 9 and the pressure adjusting means 3 are controlled to end introduction of the hot water 12 and carbon dioxide gas into the carbon dioxide gas dissolver 7.

Instead of using the carbon dioxide gas cylinder 1, it is permissible to use carbon dioxide gas obtained by condensing carbon dioxide gas in combustion gas from combustion in a combustion device. In this case, the concentration of the condensed carbon dioxide gas needs to be kept constant.

As the pressure control means 3, a pressure control valve or the like may be used. As the gas flow rate adjusting means 5 and the solution flow rate adjusting means 14, a flow rate adjusting valve or the like may be used. As the gas dissolver 7, a well known gas dissolver may be used and using the static mixer or hollow yarn membrane type dissolver enables the solubility of the dissolver to be intensified. Further, it is permissible to provide a pressure adjusting means in the downstream of the suction pump 9 of the take-in pipe A and pressure gauges before and after the same pressure adjusting means to control the pressure adjusting means by the control device 16 according to detection values from the same pressure gauges.

It is permissible to provide the bath 11 with a faucet (not shown) to pour hot water additionally or provide with a combustion device for hot water to warm up the hot water. Although FIG. 6 shows the configuration for circulating the hot water 12 to the carbon dioxide gas dissolver 7, it is possible to manufacture artificial carbonated spring by supplying hot water from a hot water supply source (not shown) to the carbon dioxide gas dissolver 7. It is permissible to arrange the carbon dioxide gas dissolvers in multi-stages in series to manufacture the artificial carbonated spring. In these cases, by disposing a measuring device on the take-out pipe from the carbon dioxide gas dissolver, the carbon dioxide gas concentration of the artificial carbonated spring discharged from the respective carbon dioxide gas dissolvers can be measured.

Figure 7:
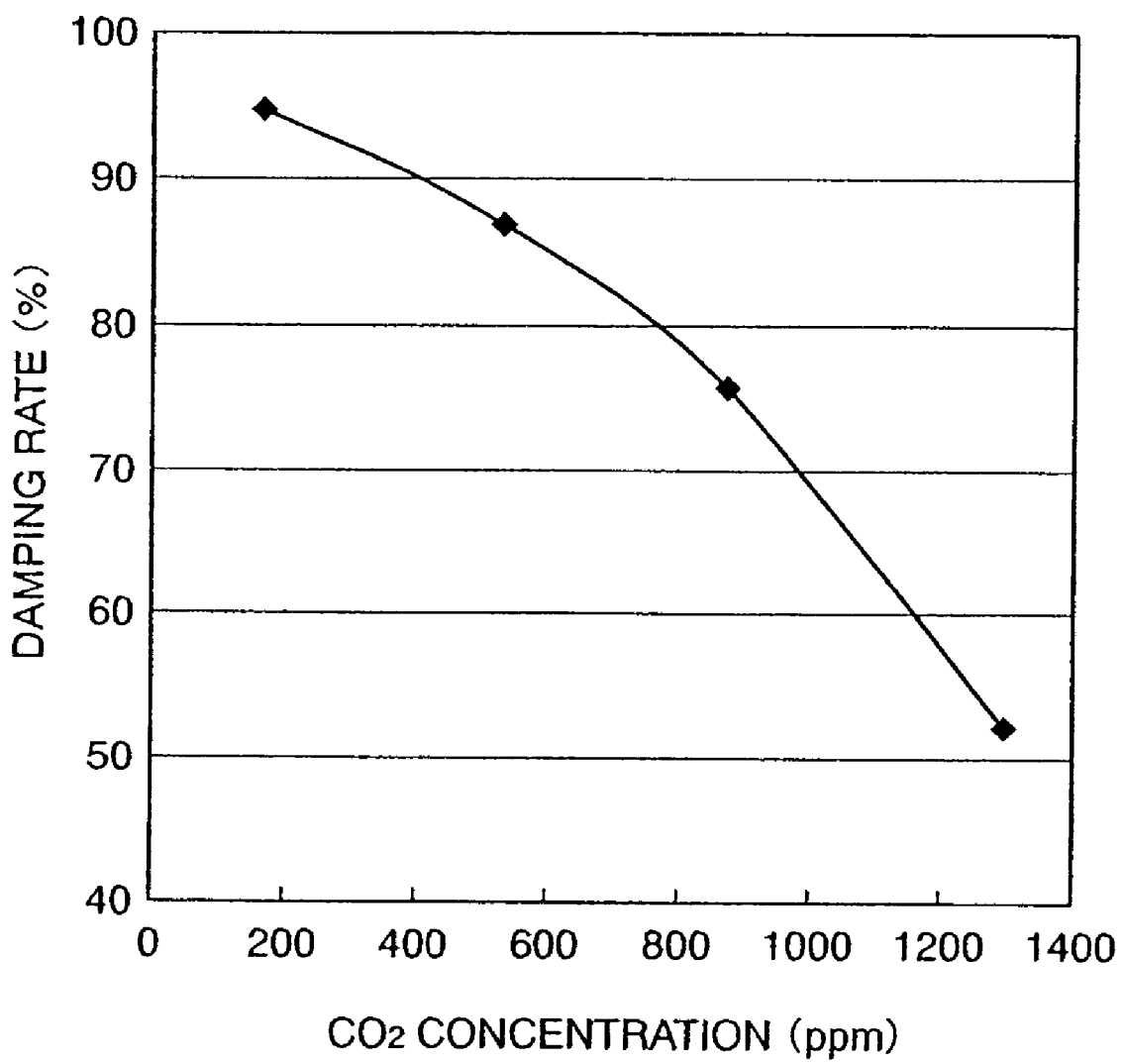
FIG. 7 is a relational diagram between damping rate and gas concentration.

FIG. 7 is a diagram showing the relational expression between the damping rate of the ultrasonic wave signal received by the ultrasonic wave receiver contained in the measuring device 13 and the measurement value of the carbon dioxide gas concentration of the artificial carbonated spring flowing through the take-in pipe A. The same relational expression is obtained under a condition that the flow rate of carbon dioxide gas introduced into the carbon dioxide gas dissolver 7 and the flow rate of hot water are constant. Because the dissolving condition changes depending on the pressure of carbon dioxide gas introduced into the carbon dioxide gas dissolver 7, the pressure of hot water, dissolving capacity of the carbon dioxide gas dissolver, temperature and pressure at the time of dissolving within the carbon dioxide gas dissolver 7 and the like, it is desirable to set up the condition for manufacturing the artificial carbonated spring preliminarily with the gas dissolver 7 and obtain the aforementioned relational expression under the set condition.

In the meantime, the present invention may be applied to manufacturing other than that of the artificial carbonated spring and in this case, it is necessary to obtain a relational expression between the quantity of bubbles and gas concentration by measuring under the manufacturing condition corresponding to the condition for manufacturing a solution.

As evident from FIG. 7, with a rise of the carbon dioxide gas concentration of the artificial carbonated spring introduced to the carbon dioxide gas dissolver (the carbon dioxide gas concentration of the artificial carbonated spring taken out of the carbon dioxide gas dissolver rises correspondingly because the dissolving condition in the dissolver is constant), the mixing amount (that is, quantity of bubbles) of undissolved gas in the artificial carbonated spring increases, so that the ultrasonic wave signal dispatched from the ultrasonic wave transmitter is damped and received by the ultrasonic wave receiver. A following will be described again and to mix the non-dissolved gas into the artificial carbonated spring, the carbon dioxide gas needs to be introduced by a flow rate not less than the maximum dissolving amount by the carbon dioxide gas dissolver 7.

Figure 8:
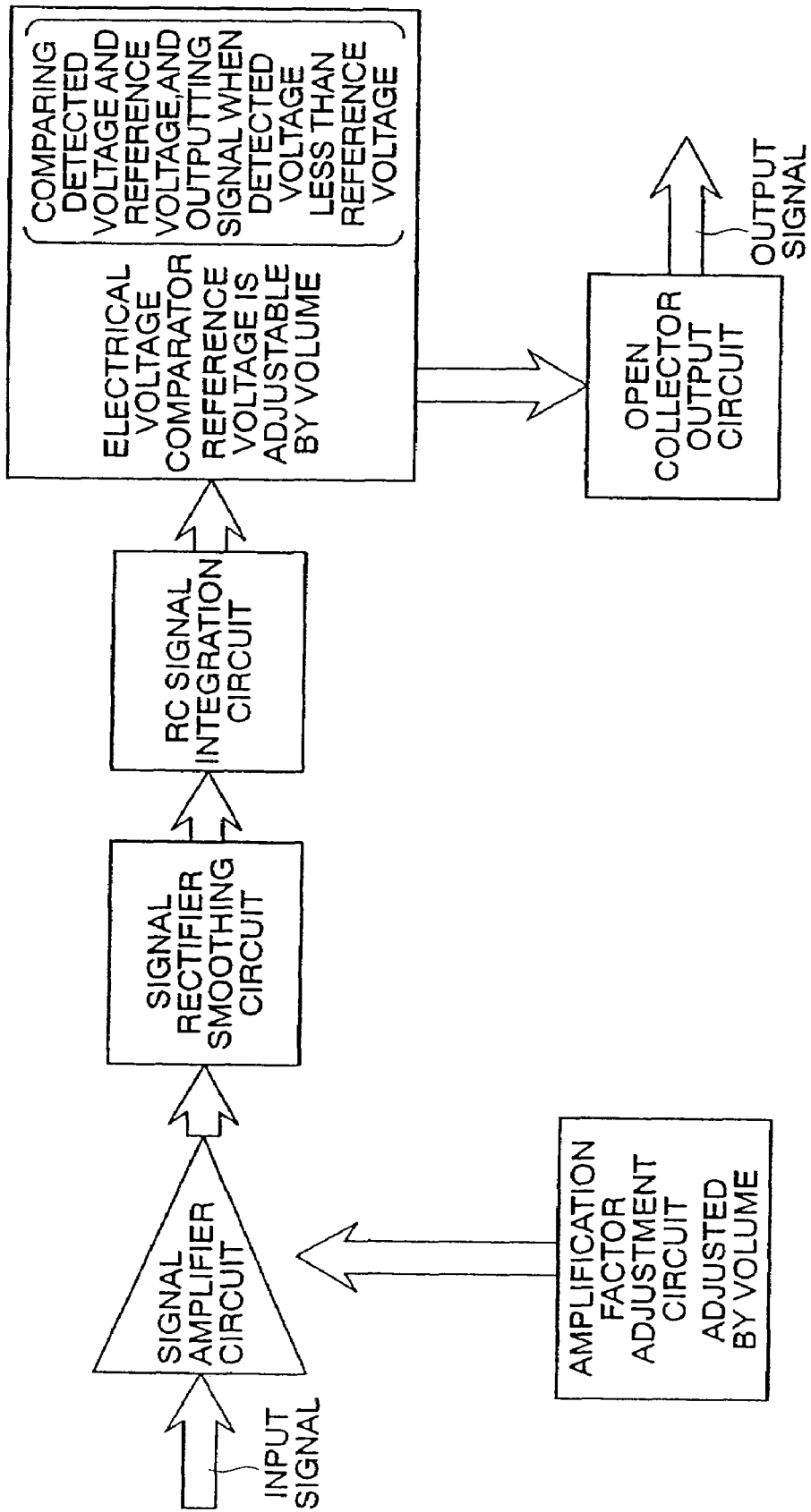
FIG. 8 is a block diagram of signal processing.

The reception signal by the ultrasonic wave transmitter incorporated in the measuring device 13 is subjected to the signal processing shown in FIG. 8. That is, after a signal received by the ultrasonic wave receiver is amplified and smoothed, signal values after a predetermined time interval are integrated and then, a value obtained by the integration (handled as a voltage value) is compared with a preliminarily set voltage value. By this comparison, it can be detected that the damping rate of the ultrasonic wave signal is a set value or less, or the carbon dioxide gas concentration of the artificial carbonated spring is a desired carbon dioxide gas concentration or more.

Although the carbon dioxide gas concentration in hot water rises with a passage of the circulation time, artificial carbonated spring having a desired carbon dioxide gas concentration can be always obtained by controlling the ON/OFF of the suction pump 9 according to the detection signal from the measuring device 13. Further, by pouring hot water directly from a supply unit such as a faucet into the bath to change the ratio between the quantity of hot water of the artificial carbonated spring and the supply amount of the carbon dioxide gas according to the detection signal of the measuring device 13, the artificial carbonated spring having a desired carbon dioxide gas concentration can be produced.

EXAMPLES

Hereinafter, the present invention having the diversified embodiments will be described more specifically with reference to the examples.

First, an example of the carbon dioxide gas adding membrane module applied to the device of the present invention will be described specifically.

(Experiment No. 1)

With polymer blend composed of styrene base thermoplastic elastomer and polypropylene (made by DAI-NIPPON PLASTICS Co., Ltd., product name MK resin MK-2F (Tg=−35° C., composition ratio: (S)-(EB)-(S) tri-block copolymer 50 mass portion, composed of polymer (EB) obtained by hydrogenating styrene polymer (S) and butadiene polymer, as styrene base thermoplastic elastomer and atactic polypropylene 50 mass portion as polyolefin) as a material for a nonporous layer and polyethylene (made by TOSOH CORPORATION, product name: NIPORON HARD 5110) as a material for a porous layer, a three-layered composite hollow yarn membrane shown in FIG. 5 having the outside diameter of 300 μm, the inside diameter of 180 μm and the nonporous layer thickness of 2 μm was manufactured.

The carbon dioxide gas permeating amount of this composite hollow yarn membrane was $3.3 \times 10^{-2}$ m$^3$/m$^2$·hr·0.1 MPa and the vapor permeating amount was 22 g/m$^2$·hr·0.1 MPa.

The carbon dioxide gas adding hollow yarn membrane module shown in FIG. 4 was produced using the obtained composite hollow yarn membrane such that the hollow yarn membrane area was 0.71 m$^2$, the volume was $1.6 \times 10^{-4}$ m$^3$ and the membrane density was 4438 m$^2$/m$^3$. An intermittent operation of supplying water of 40° C. by a flow rate of 5 l/min to the hollow portion in the hollow yarn membrane for three minutes while supplying carbon dioxide gas with a pressure of 0.36 MPa at 1.25 l/min and then interrupting the supplies of carbon dioxide gas and water for 57 minutes, which is a cycle of an hour was carried out continuously for 1000 hours.

When 20% the effective length of the hollow yarn membrane was submerged in water, the drain discharge port was opened for first one minute of 57-minute stop time to discharge drain using remaining carbon dioxide gas pressure. All drain in the module was discharged in the open time of a minute.

Table 1 shows the generation amount per unit time of drain permeated to the carbon dioxide gas supply side, the frequency of drain discharge and the use amount of carbon dioxide gas.

(Experiment No. 2)

With thermoplastic segmented polyurethane (made by Thermedics Inc. product name: Tecoflex EG80A) as the material of the nonporous layer and polyethylene (made by Tosoh Corporation, product name: Niporon Hard 5110) as the material of the porous layer, the three-layered composite hollow yarn membrane shown in FIG. 5 having the outside diameter of 300 μm, the inside diameter of 180 μm and the nonporous layer thickness of 15 μm was produced.

The carbon dioxide gas permeating amount of the obtained composite hollow yarn membrane was $1.6 \times 10^{-2}$ $m^3/m^2 \cdot hr \cdot 0.1$ MPa and the vapor permeating amount was $4.23 \times 10^2$ $g/m^2 \cdot hr \cdot 0.1$ MPa.

The same carbon dioxide gas adding hollow yarn membrane as Experiment No. 1 was produced using this membrane and the same operation as Experiment No. 1 was carried out.

Table 1 shows the generation amount per unit time of drain permeating the carbon dioxide gas supply side, the frequency of drain discharge and the use amount of carbon dioxide gas.

(Experiment No. 3)

A composite hollow yarn membrane having the same three-layered structure as Experiment No. 2 except that the thickness of the nonporous layer was 1 μm was produced.

The carbon dioxide gas permeating amount of the obtained composite hollow yarn membrane was $2.6 \times 10^{-1}$ $m^3/m^2 \cdot hr \cdot 0.1$ MPa and the vapor permeating amount was $6.8 \times 10^3$ $g/m^2 \cdot hr \cdot 0.1$ MPa.

The same carbon dioxide gas adding hollow yarn membrane module as Experiment No. 1 was produced using this membrane and the same operation as Experiment No. 1 was carried out.

Table 1 shows the generation amount per unit time of drain permeating to the carbon dioxide gas supply side, the frequency of drain discharge and the use amount of carbon dioxide gas.

TABLE 1

| | Drain amount ml/min | Drain discharge frequency Time/1000 hr | Carbon dioxide gas use amount kg/1000 hr |
|---|---|---|---|
| Experiment No. 1 | 0.003 | 12 | 7.5 |
| Experiment No. 2 | 0.08 | 320 | 7.9 |
| Experiment No. 2 | 0.77 | 3000 | 10.5 |

By using the carbon dioxide gas adding membrane module of the present invention as shown in Table 1, the consumption of carbon dioxide gas could be reduced.

The carbon dioxide gas adding membrane module of the present invention enables carbon dioxide gas to be added into water even when hot water is fed because a membrane whose carbon dioxide gas permeating amount at 25° C. was $1 \times 10^{-3}$ to 1 $m^3/m^2 \cdot hr \cdot 0.1$ MPa and whose vapor permeating amount at 25° C. was $1 \times 10^3$ $g/m^2 \cdot hr \cdot 1.0$ MPa or less was used. Because the amount of vapor permeating the membrane is small and drain is unlikely to be deposited on the gas side, the frequency of drain discharges and the amount of carbon dioxide gas discharge into the atmosphere at the time of drain discharge can be reduced. Accordingly, the carbon gas additive water can be obtained at a high efficiency for a long time, so that the module can be applied widely to applications for adding carbon dioxide gas to low temperature water, normal temperature water and further high temperature water.

Further, because the membrane density of the carbon dioxide gas adding module is in a range of 2000 to 7000 $m^2/m^3$, drain can be discharged smoothly while maintaining the dissolving efficiency of the carbon dioxide gas high.

If carbon dioxide gas is dissolved after water is heated to 30° C. to 50° C. preliminarily, carbon dioxide gas can be dissolved efficiently.

Next, a typical embodiment of the carbonated spring manufacturing device of the present invention will be described. The carbon dioxide gas concentration of the carbonated spring was obtained according to Tillman's expression by measuring alkaline degree and pH.

(Experiment No. 4)

Carbonated spring was produced with the circulation type device shown in FIG. 1. The carbon dioxide gas pressure was controlled to 0.4 MPa with a pressure control valve. As a flow meter, an electronic mass flow meter (CMS0020) made by Yamatake Hanewel Co., Ltd. was used and as a flow control valve, a mass flow control valve (MODEL 2203) made by KOFLOK K.K. was used to control the carbon dioxide gas flow rate to 1.0 l/min (converted under 20° C.). As a dissolver, non-used hollow yarn module product made with a three-layered composite hollow yarn membrane (made by Mitsubishi Rayon Co., Ltd.) whose membrane area was 0.6 $m^2$ was used. Hot water at 40° C. was poured into the bath by 10 l and the hot water was returned to the bath by 5 l every minute by means of a suction pump.

Table 2 shows the result obtained 10 minutes after circulation. The first time in Table 2 indicates the result collected first in the experiment and the second time indicates the result collected after the first time. Both indicated the same carbon dioxide concentration.

(Experiment No. 5)

The flow control valve of Experiment No. 4 was released to control the carbon dioxide gas supply amount with pressure. The pressure was controlled to 0.15 MPa. Table 2 shows the result thereof. The carbon dioxide gas concentration was low at the first time and high at the second time.

TABLE 2

| | Frequency | Carbon dioxide gas concentration (mg/l) |
|---|---|---|
| Experiment No. 4 | First time | 1310 |
| | Second time | 1310 |
| Experiment No. 5 | First time | 1040 |
| | Second time | 1230 |

(Experiment No. 6)

This experiment was executed in the same manner as in Experiment No. 4 except that the flow rate of the circulation pump was 1 l every minute, that is, the ratio between the flow rate of the circulation pump and the flow rate of the carbon dioxide gas was set to 1. At the first time, the carbon dioxide gas concentration dropped to 700 mg/l, so that the dissolving efficiency was reduced remarkably.

(Experiment No. 7)

Carbonated spring was produced with the one-pass type device shown in FIG. 3. The carbon dioxide gas pressure was controlled to 0.4 MPa with the pressure control valve. With the electronic mass flow meter CMS0020 made by Yamatake Hanewel Co., Ltd. as a flow meter and the float controller MODEL 2203 made by KOFLOK K.K. as a flow control valve, the carbon dioxide gas flow rate was controlled to 5.0 l/min (converted under 25° C.).

A hollow yarn module produced with the three-layered composite hollow yarn membrane (made by Mitsubishi Rayon Co., Ltd.) whose membrane area was 2.4 m$^2$ was used as a dissolver. Water at 40° was fed to the dissolver at 5 l/min. Table 3 shows the result thereof. Carbon dioxide gas concentration was stabilized about two minutes after water was fed first.

(Experiment No. 8)

The flow control valve of Experiment No. 7 was opened to control the carbon dioxide gas supply amount with a pressure. The pressure was controlled to 0.28 MPa. Table 3 shows the result thereof. The carbon dioxide gas concentration in the initial period of water feeding was unstable as compared with Example 4, so that the carbon dioxide gas concentration was not stabilized even if 10 minutes passed after water was fed first.

TABLE 3

| | Water feeding time | | | | | |
|---|---|---|---|---|---|---|
| | 1 | 2 | 3 | 5 | 7 | 10 |
| Experiment No. 7 | 1190 | 1210 | 1210 | 1210 | 1210 | 1210 |
| Experiment No. 8 | 610 | 820 | 940 | 1100 | 1160 | 1200 |

Carbon dioxide gas concentration (mg/l)

(Experiment No. 9)

The same operation as Experiment No. 4 was carried out with a module used for 500 hours and its result was compared with the result of Experiment No. 4 using the unused product. Table 4 shows the result thereof. The same performance as the unused product was obtained.

(Experiment No. 10)

The same operation as Experiment No. 5 was carried out with a module used for 500 hours and its result was compared with the result of Experiment No. 5 using the unused product. Table 4 shows the result thereof. The carbon dioxide gas concentration dropped as compared with the unused product.

TABLE 4

| | Use time (min) | Carbon dioxide gas concentration (mg/l) |
|---|---|---|
| Experiment No. 4 | 0 | 1310 |
| Experiment No. 9 | 500 | 1290 |
| Experiment No. 5 | 0 | 1040 |
| Experiment No. 10 | 500 | 980 |

Next, an example about the dissolving efficiency of carbon dioxide gas will be described specifically. The carbon dioxide concentration in carbonated spring was obtained according to Tiliman's expression by measuring alkaline degree and pH. Table 5 shows a summarized result. Meanwhile, the dissolving efficiency in Table 5 was obtained from "dissolving efficiency (%)=carbon dioxide gas dissolving amount in carbonated spring/amount of used carbon dioxide gas×100".

(Experiment No. 11)

Carbonated spring was produced with the circulation type device shown in FIG. 2. The carbon dioxide gas pressure was controlled to 0.4 MPa with the pressure control valve. Two mass flow control valves (MODEL 2203) made by KOFLOK K.K. were used as the flow control valves and the carbon dioxide gas flow rate of one of them was adjusted to 2.0 l/min (converted under 20°) while the other was adjusted to 0.5 l/min (converted under 20°). As the dissolver, a hollow yarn module produced with the three-layered composite hollow yarn membrane (made by Mitsubishi Rayon Co., Ltd.) whose membrane area was 0.6 m$^2$ was used. Hot water at 40° C. was poured into the bath up to 10 l and the hot water was returned to the bath by 5 l every minute by means of the circulation pump.

An electromagnetic valve was opened for carbon dioxide gas to flow to the flow control valve adjusted to 2.0 l/min at the startup of manufacturing while the other valve was closed. Up to the end 2 minutes to 10 minutes after, the electromagnetic valve was opened for carbon dioxide gas to flow to the flow control valve adjusted to 0.5 l/min while the other valve was closed. Table 5 shows its result.

(Experiment No. 12)

This experiment was carried out in the same manner as in Experiment No. 11 except that the carbon dioxide gas was fed constantly at 1.0 l/min (converted under 20° C.) during manufacturing. Table 5 shows its result. The dissolving efficiency was lower than that of Experiment No. 11.

(Experiment No. 13)

This experiment was executed in the same manner as in Experiment No. 11 except that carbon dioxide gas was fed constantly at 0.5 l/min (converted under 20° C.) during manufacturing. Table 5 shows its result. Although the dissolving efficiency was high, the carbon dioxide gas concentration was lower than that of Experiment No. 11.

(Experiment No. 14)

This experiment was executed in the same manner as in Experiment No. 11 except that carbon dioxide gas was fed constantly at 2.0 l/min (converted under 20°) during manufacturing. Table 5 shows its result. Although a high concentration carbonated spring could be obtained in a short time, the dissolving efficiency was worsened remarkably.

TABLE 5

| | Manufacturing time (min) | Carbon dioxide gas concentration (mg/l) | Dissolving efficiency (%) |
|---|---|---|---|
| Experiment No. 11 | 10 | 1310 | 79 |
| Experiment No. 12 | 10 | 1300 | 65 |
| Experiment No. 13 | 10 | 1080 | 98 |
| Experiment No. 14 | 8 | 1320 | 43 |

Finally, an example using the manufacturing device for the artificial carbonated spring shown in FIG. 6 will be described specifically.

(Experiment No. 15)

Hot water at 40° C. was poured into the bath by 10 l and 20 l and the circulation pump (5 l/min), a hollow yarn module produced with the three-layered composite hollow yarn membrane (made by Mitsubishi Rayon Co., Ltd.) whose membrane area was 0.6 $m^2$, a carbon dioxide gas cylinder, a carbon dioxide gas flow control valve and a measuring device for detecting bubbles with ultrasonic wave were connected in the order indicated in FIG. 6. The flow rate of carbon dioxide gas was set to 1.5 l/min, the maximum value (when water is circulated) of a reception signal by the measuring device was set to 4.8 mV and the threshold of a detection signal dispatching was set to 3.1 mV (calculated from the damping rate 65% which provides 1100 mg/l according to FIG. 7) and then, the circulation pump was operated. When the detection signal was dispatched, the operation was stopped and the carbon dioxide gas concentration of the produced artificial carbonated spring was measured with an ion electrode type carbon dioxide gas measuring device (made by To a Denpa: IM40).

As a result, artificial carbonated spring having a target carbon dioxide gas concentration of 1100 mg/l shown in Table 6 was obtained.

TABLE 6

| Quantity of hot water (l) | Setting concentration (ppm) Damping rate (%) | Measured value of carbon dioxide gas concentration (ppm) |
|---|---|---|
| 10 | 1100 65% | 1120 |
| 20 | 1100 65% | 1100 |

EFFECT OF THE INVENTION

According to the carbonated spring manufacturing device of the present invention, which comprises a carbon dioxide gas dissolver and a circulation pump, water in a bath is circulated by the circulation pump through the carbon dioxide gas dissolver and carbon dioxide gas is supplied into the carbon dioxide gas dissolver so as to dissolve carbon dioxide gas into water. By raising the carbon dioxide gas concentration in water gradually, carbonated spring having a high concentration is manufactured. By retarding the supply velocity of the carbon dioxide gas in the latter half period as compared with the former half period of the manufacturing time, high concentration carbonated spring can be obtained effectively.

According to the carbonated spring manufacturing method of the present invention, carbon dioxide gas supplied from a carbon dioxide gas cylinder is controlled in terms of the gas flow rate to allow it to flow into the dissolver and dissolved into hot water. Consequently, a carbonated spring manufacturing method capable of obtaining an unchanging carbonic acid concentration can be provided.

According to the carbon dioxide gas adding membrane module of the present invention, because the carbon dioxide gas permeating amount and vapor permeating amount under a predetermined temperature are set in a predetermined range, carbon dioxide gas can be added into water even when it is fed to hot water. Particularly, because the quantity of vapor permeating the membrane is small and drain is unlikely to be deposited on the gas side, the frequency of drain discharges and the quantity of carbon dioxide to be discharged into the atmosphere at the time of drain discharge can be reduced. Further, because carbon dioxide gas added water can be obtained at a high efficiency in a long period, this module can be applied widely to applications for adding carbon dioxide gas to low temperature water, normal temperature water and high temperature water.

Further, because the membrane density of the membrane module is set in a range of 2000 to 7000 $m^2/m^3$, drain can be discharged smoothly while maintaining the dissolving efficiency of carbon dioxide gas high. When carbon dioxide gas is dissolved after water is heated to 30° C. to 50° C. preliminarily, carbon dioxide gas can be dissolved effectively.

The invention claimed is:

1. A device for manufacturing a gas dissolved solution, comprising:
   a gas supply source having gas flow rate adjusting means;
   a gas dissolver in which gas and solution are to be introduced from the gas supply source;
   solution flow rate adjusting means for controlling the flow rate of the solution introduced into the gas dissolver to be constant; and
   a take-out pipe for taking out a solution from the gas dissolver, the manufacturing device further comprising:
   a measuring device for measuring the quantity of gas bubbles existing in the take-out pipe; and
   a control device for computing the gas concentration of the solution based on a relational expression between the quantity of bubbles and gas concentration measured preliminarily under a condition that the solution flow rate and gas flow rate are constant and a measured value from the measuring device and controlling the gas flow rate adjusting means and/or the solution flow rate adjusting means based on the computation result.

2. The device for manufacturing a gas dissolved solution according to claim 1, wherein the measuring devices are an ultrasonic wave transmitter and an ultrasonic wave receiver disposed across the take-out pipe.

3. The device for manufacturing a gas dissolved solution according to claim 2, wherein the gas dissolver is a static mixer.

4. The device for manufacturing a gas dissolved solution according to claim 1, wherein the gas dissolver is a hollow yarn membrane type dissolver.

5. The device for manufacturing a gas dissolved solution according to claim 1, further comprising a storage bath for storing a solution discharged from the take-out pipe, wherein liquid in the storage bath is circulated to the gas dissolver through the solution flow rate adjusting means.

6. The device for manufacturing a gas dissolved solution according to claim 1, wherein the gas is carbon dioxide gas while the solution is artificial carbonated spring.

7. The device for manufacturing a gas dissolved solution according to claim 2, wherein the gas dissolver is a hollow yarn membrane type dissolver.

8. The device for manufacturing a gas dissolved solution according to claim 2, further comprising a storage bath for storing a solution discharged from the take-out pipe, wherein liquid in the storage bath is circulated to the gas dissolver through the solution flow rate adjusting means.

* * * * *